(12) United States Patent
Bruehwiler et al.

(10) Patent No.: US 8,876,780 B2
(45) Date of Patent: Nov. 4, 2014

(54) ATTACHABLE NEEDLE CHANGING DEVICE FOR MEDICAMENT DELIVERY DEVICE

(75) Inventors: Michel Bruehwiler, Newton, MA (US); Cole Constantineau, Cambridge, MA (US); Ryan Schoonmaker, San Marcos, CA (US); Margaret Taylor, Groton, MA (US); James S. Bates, Sparta, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 313 days.

(21) Appl. No.: 13/206,469

(22) Filed: Aug. 9, 2011

(65) Prior Publication Data

US 2012/0041385 A1    Feb. 16, 2012

Related U.S. Application Data

(60) Provisional application No. 61/344,535, filed on Aug. 16, 2010.

(51) Int. Cl.
*A61M 5/32* (2006.01)
*A61M 5/34* (2006.01)
*A61M 5/00* (2006.01)

(52) U.S. Cl.
CPC .............. *A61M 5/002* (2013.01); *A61M 5/343* (2013.01); *A61M 5/34* (2013.01); *A61M 2005/004* (2013.01)
USPC ............ 604/198; 604/263; 604/176; 604/366

(58) Field of Classification Search
USPC ........................ 604/198, 263, 176; 206/366
See application file for complete search history.

(56) References Cited

U.S. PATENT DOCUMENTS

| | | | |
|---|---|---|---|
| 5,829,589 | A | 11/1998 | Nguyen et al. |
| 5,971,966 | A | 10/1999 | Lav |
| 6,616,616 | B2 | 9/2003 | Fritz et al. |
| 6,783,537 | B1 | 8/2004 | Kuhr et al. |
| 7,314,464 | B2 | 1/2008 | Giambattista et al. |
| 7,645,264 | B2 | 1/2010 | Marsh et al. |
| 2002/0020646 | A1 | 2/2002 | Groth et al. |

FOREIGN PATENT DOCUMENTS

| | | |
|---|---|---|
| WO | WO 01/93927 A1 | 12/2001 |
| WO | WO 2004/004812 A1 | 1/2004 |
| WO | WO 2007/143323 A1 | 12/2007 |
| WO | WO 2009/016161 A1 | 2/2009 |

*Primary Examiner* — Edelmira Bosques
(74) *Attorney, Agent, or Firm* — Roylance, Abrams, Berdo and Goodman, LLP

(57) ABSTRACT

An attachable needle storage device is provided with a main body and a rotatable sleeve and a plurality of new needles stored within the sleeve, a leaf spring to direct each needle into a circumferential position of the pen body when rotated, and a ramp to move the needle into an axial position of the pen body when retracted or pulled rearward by the user. The attachable needle storage device is configured to attach to a pen device in a manner substantially the same as a conventional needle hub. In doing so, the rotation of the sleeve can be used to rotate a new needle onto a shuttle, and the retraction of the device can be used to cause a ramp to engage the needle and needle hub, moving the needle toward the axial position of the pen body and the septum. Once under the septum, the user continues pulling the device rearward, such that the needle is then moved rearward, pierces the septum of the medicament cartridge and exposes the distal end of the needle for injection. After use, a needle shield is used to unlock a compressed spring, which is configured to pull the needle from the septum, and return the device to the transport state, after which the previous steps can be repeated.

18 Claims, 20 Drawing Sheets

US 8,876,780 B2

ATTACHABLE NEEDLE CHANGING DEVICE FOR MEDICAMENT DELIVERY DEVICE

CROSS-REFERENCE TO RELATED APPLICATIONS

This application claims the benefit under 35 U.S.C. §119 (e) of a U.S. provisional patent application of Michel Bruehwiler et al. entitled "Attachable Needle Changing Device For Medicament Delivery Device", Ser. No. 61/344,535, filed on Aug. 16, 2010, the entire content of said application being incorporated herein by reference.

FIELD OF THE INVENTION

The present invention relates to an attachable needle changing device for containing and dispensing one or more new needles, and for receiving and securely storing used needles after use. More particularly, the present invention relates to an attachable needle changing device for rotatably and retractably attaching to a medicament delivery device and providing, through such rotatable and retractable attachment, containment and dispensing of new needles, and containment and storage of used needles, for the attached medicament delivery device.

BACKGROUND OF THE INVENTION

In certain circumstances, it is desirable to inject medication directly into human tissue. Typically, syringes or pen injection devices are used to inject medicaments into tissue areas, such as the intramuscular tissue layer, the subcutaneous tissue layer, and the intradermal tissue layer. The assembly and operation of such a pen injection device is described in U.S. Pat. No. 7,645,264, issued on Jan. 12, 2010, the entire contents of which are hereby incorporated herein by reference.

Pen injection devices, such as the exemplary drug delivery pen 10 as shown in FIG. 1, provide the user a convenient way to carry a medicament supply. All of the required features and components for at least a single use are provided in the assembly, and in most cases, provide for multiple uses. To do so, the pen 10 typically comprises a dose knob/button 24, an outer sleeve 13, and a cap 21. The cap 21 covers a proximal end of the pen 10 and an injection needle attached thereto, and is used by the user to securely hold the drug delivery pen 10 in a shirt pocket, purse or other suitable location. The dose knob/button 24 allows a user to set the dosage of medication to be injected, and the outer sleeve 13 contains the driving mechanisms and supply, and further provides a gripping surface for the user to grip when injecting medication.

FIG. 2A is an exploded view of the exemplary drug delivery pen 10 shown in FIG. 1, and typical components contained therein. At a distal end, the dose knob/button 24 is provided and has a dual purpose. The dose knob/button 24 is used to both set the dosage of the medication to be injected and to inject the dosed medicament via the lead screw 7 and stopper 15 through the medicament cartridge 12, which is attached to the drug delivery pen through a lower housing 17. In standard drug delivery pens, the dosing and delivery mechanisms are all found within the outer sleeve 13 and are not described in greater detail herein as they are understood by those knowledgeable of the prior art. The distal movement of the plunger or stopper 15 within the medicament cartridge 12 causes medication to be forced into the needle 11 of the hub 20. The medicament cartridge 12 is sealed by septum 16, which is punctured by a septum penetrating needle cannula 18 located within the hub 20. The hub 20 is preferably screwed onto the lower housing 17, although other attachment means can be used.

FIGS. 2B and 2C are perspective views of the pen needle of FIG. 2A in greater detail. As shown in FIG. 2B, the pen needle includes the hub 20 disposed at a non-patient end thereof which includes a plurality of ribs 64 for engagement with anti-rotation/retaining structures. In addition, protrusion 68 extends from a patient end of the hub 20 and the patient needle 11 extends from the protrusion 68. The septum-penetrating needle cannula 18 disposed within the non-patient end of the hub 20 fluidly communicates with the patient needle 11. Further, as shown in FIG. 2C, the interior of the non-patient end of the hub 20 includes threads 72 for connection with the lower housing 17. FIGS. 2A-2C illustrate one example of a pen needle.

To protect a user, or anyone who handles the drug delivery pen 10, an outer cover 69, which attaches to the hub 20, covers the hub when not in use. An inner shield 59 covers the patient needle 11 within the outer cover 69. The inner shield 59 can be secured to the hub 20 to cover the patient needle 11 by any suitable means, such as an interference fit or a snap fit. The cap 21 fits snugly against outer sleeve 13 to allow a user to securely carry the drug delivery pen 10. At a time of use, the cap 21, outer cover 69 and inner shield 59 are removed to expose the hub 20.

The medicament cartridge 12 is typically a tube sealed at one end with the septum 16 and sealed at the other end with the stopper 15. The septum 16 is pierceable by the septum penetrating cannula 18 in the hub 20, but does not move with respect to the medicament cartridge 12. The stopper 15 is axially displaceable within the medicament cartridge 12 to deliver the desired medicament amount while maintaining a fluid tight seal.

A pen needle, which includes the hub 20, needle 11, outer cover 69 and inner shield 59, is typically used for a single injection and is then disposed of. New pen needles are packaged individually and disposed loose in a container, such as a box or carton. Each pen needle is sealed in a package formed by the outer cover with a label covering the opening in the outer cover to identify the pen needle and provide a sterility barrier. However, containers of such packaged new pen needles do not include means for easily dispensing the new pen needles or containing used pen needles. Accordingly, a need exists for a storage assembly that easily dispenses new pen needles and stores both new and used pen needles.

Additionally, existing pen needle containers are configured to store a large number of packaged new pen needles. The large number of packaged new pen needles causes these containers to be large and bulky, such that the containers are not conducive to being carried by the user. Accordingly, a need exists for a storage assembly that is conveniently carried by a user.

Further, typical insulin delivery pens require users to change needles after each injection. These needles and needle changes can take up to six user steps to install and remove a needle from the pen device. Further, in doing so, the user is vulnerable to accidental needle sticks when manipulating the needle. Accordingly, a need exists for a pen needle storage device that assists in needle installation and removal.

SUMMARY OF THE INVENTION

In accordance with aspects of exemplary embodiments of the present invention, the above and other problems are substantially solved by providing an attachable needle storage device for rotatably and retractably attaching to a medicament delivery device and providing, through such rotatable and retractable attachment, containment and dispensing of new needles, and containment and storage of used needles, for the attached medicament delivery device.

In accordance with an aspect of the present invention, the attachable needle storage device is configured to be attached to a distal end of a pen device and is provided with an array of contained, unexposed new needles for use, and features to store unexposed pen needles after use.

In accordance with another aspect of the present invention, the attachable needle storage device is provided with an exterior twisting dial or rotatable sleeve for the user to advance a fresh needle to a delivery position without exposing any part of the needle.

In accordance with another aspect of the present invention, the attachable needle storage device, when rotated to the delivery position, is configured to be retracted or pulled in the proximal direction of the pen body. As the user pulls back on the attachable needle storage device, the new needle is first moved to an axial position of the pen body by engaging a ramp, and is next moved rearward to pierce the pen cartridge septum and is gradually exposed at only an opposite end for insertion into the delivery site.

In accordance with another aspect of the present invention, the attachable needle storage device, when delivery is complete, is configured to spring back or be pushed back into the initial state, removing the needle from the pen septum and sheathing the exposed distal end of the needle, and moving the needle away from the axial position of the pen body for enclosed storage in the array from which the new needle was removed. The user may now advance the next new needle into the delivery position and start the process again.

In accordance with another aspect of the present invention, the attachable needle storage device is provided with a main body and a rotatable sleeve and a plurality of unexposed new needles stored within the sleeve, a leaf spring to direct each new needle into a circumferential position of the pen body when rotated, and a ramp to move the new needle into an axial position of the pen body when retracted. The attachable needle storage device is configured to attach to a pen device in a manner substantially the same as a conventional needle hub. In doing so, the rotation of the sleeve can be used to rotate a new needle onto a shuttle, and the retraction or sliding of the entire device can be used to cause the ramp to engage the needle and needle hub, moving it horizontally toward the axial position of the pen body and the septum via a needle tray. Once under the septum, the user continues pulling the entire device rearward and posts on the ramp unsnap a needle tray such that the shuttle, needle and needle hub, and needle tray are moved rearward as pulled engaging the septum and exposing the distal end of the needle for injection. The device is secured in this position for use by at least one detent against a compressed spring and after use, a needle shield is used to unlock the detent and the compressed spring, which is configured to pull the needle from the septum, and return the device to the transport state, where the previous steps can be repeated.

In accordance with another aspect of the present invention, a method of changing a needle is provided by first attaching the attachable needle storage device to a pen device in a manner substantially the same as a conventional needle hub, rotating a rotatable sleeve to rotate an unexposed new needle onto a shuttle, retracting or pulling the entire device rearward to cause a ramp to engage the needle hub and move the needle and needle hub horizontally toward the axial position of the pen body and the septum via a needle tray. Once under the septum, the user continues pulling the entire device rearward and posts on the ramp unsnap a needle tray such that the shuttle, needle and needle hub, and needle tray are moved rearward as pulled engaging the septum and exposing the distal end of the needle for injection. The device is secured in this position for use by at least one detent against a compressed spring and after use, a needle shield is used to unlock the detent and the compressed spring, which is configured to pull the needle from the septum, and return the device to the transport state, where the previous steps can be repeated.

These and other objects, advantages, and salient features of the invention will become apparent from the following detailed description, which, taken in conjunction with the annexed drawings, discloses exemplary embodiments of the invention.

BRIEF DESCRIPTION OF THE DRAWINGS

The above benefits and other advantages of the various embodiments of the present invention will become more apparent from the following detailed description of exemplary embodiments of the present invention and from the accompanying figures, in which.

DETAILED DESCRIPTION OF THE EXEMPLARY EMBODIMENTS

Figure 1:
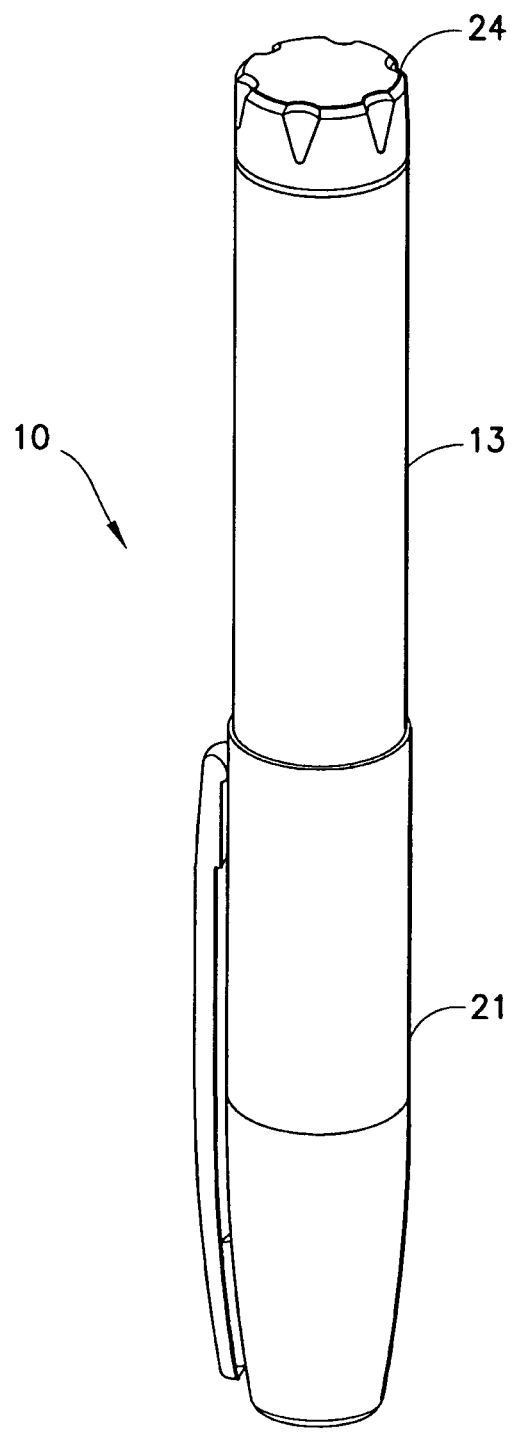
FIG. 1 is a perspective view of an assembled drug delivery pen for use with exemplary embodiments of the present invention.

Exemplary embodiments of the present invention provide a system and method for changing needles in a contained, efficient, and user-friendly manner. In an exemplary embodiment of the present invention, an attachable needle storage device is provided with a main body and a rotatable sleeve, and a plurality of new needles stored fully enclosed within the sleeve, a leaf spring to direct each new needle into a circumferential position of the pen body when rotated, and a ramp to move the new needle into an axial position of the pen body when retracted or pulled rearward. The attachable needle storage device is configured to attach to a pen device in a manner substantially the same as a conventional needle hub. The rotation of the sleeve can then be used to rotate an enclosed new needle onto a shuttle, and the retraction or pulling rearward of the device can be used to cause the ramp to engage the needle and needle hub, moving the needle horizontally towards the axial position of the pen body and the septum via a needle tray. Once under the septum, the user continues pulling the entire device rearward and posts on the ramp unsnap a needle tray such that the shuttle, needle and needle hub, and needle tray are moved rearward as pulled engaging the septum and exposing the distal end of the needle for injection. The device is secured in this position for use by at least one detent against a compressed spring and after use, a needle shield is used to unlock the detent and the compressed spring, which is configured to pull the needle from the septum, and return the device to the transport state, where the previous steps can be repeated.

In an exemplary embodiment, an array of fully enclosed needles are contained within the pen device, attached to the end of a typical pen device, or likewise integrated into a specially designed delivery device. The device itself has an exterior twisting dial for the user to advance a new needle to the delivery position. The device can then be retracted or pulled by the user in the proximal direction of the pen body. As the user pulls back on the device, the enclosed new needle is moved to an axial position of the pen body and into an opening allowing rearward travel, where the proximal end of the enclosed new needle pierces the pen cartridge septum as the needle is pulled rearward, and the distal end of the needle is gradually exposed for insertion into the delivery site. The device is secured in this position for use by at least one detent against a compressed spring and after use, a shield is provided to unlock the device such that the device springs back into the initial state, removing the needle from the pen septum and sheathing the distal end of the needle. The user may now advance the next needle into the delivery position and start the process again.

In an exemplary embodiment, needles within the device are stored within an annularly expanded part that protrudes from the outer surface of the device to form a needle advancement dial or sleeve. The needle hubs fit within slots, or fork-like arms in the rotatable sleeve, and as the user rotates the sleeve, a new needle is forced onto the shuttle through contact with a leaf spring while a used needle is moved from the shuttle to an open slot or fork in the annular component. To facilitate the transfer from the storage slots or forks to the shuttle, the leaf spring remains in contact with the needle and needle hubs as they are rotated past the leaf spring. As the user turns the sleeve, the new needle being transferred to the shuttle deflects the leaf spring away from the shuttle. Without the counter force provided by this leaf spring, the shuttle, under spring force itself, expels the used needle into a slot or fork on the annular piece.

Once a new needle is placed on the shuttle, the user then retracts or pulls the device proximally up the pen body. This vertical motion causes a ramp within the device to engage the needle and needle hub now in the shuttle, moving the needle horizontally toward the axial position of the pen body and in alignment with a septum of a medicament cartridge. Once under the septum, the user continues pulling the device vertically and posts on the ramp unsnap a needle tray such that the shuttle, needle and needle hub, and needle tray are moved rearward as pulled engaging the septum and exposing the distal end of the needle for injection. The device is secured in this position for use by at least one detent against a compressed spring and after use, a needle shield is used to unlock the detent and the compressed spring, which is configured to pull the needle from the septum, and return the device to the transport state, where the previous steps can be repeated.

Figure 3:
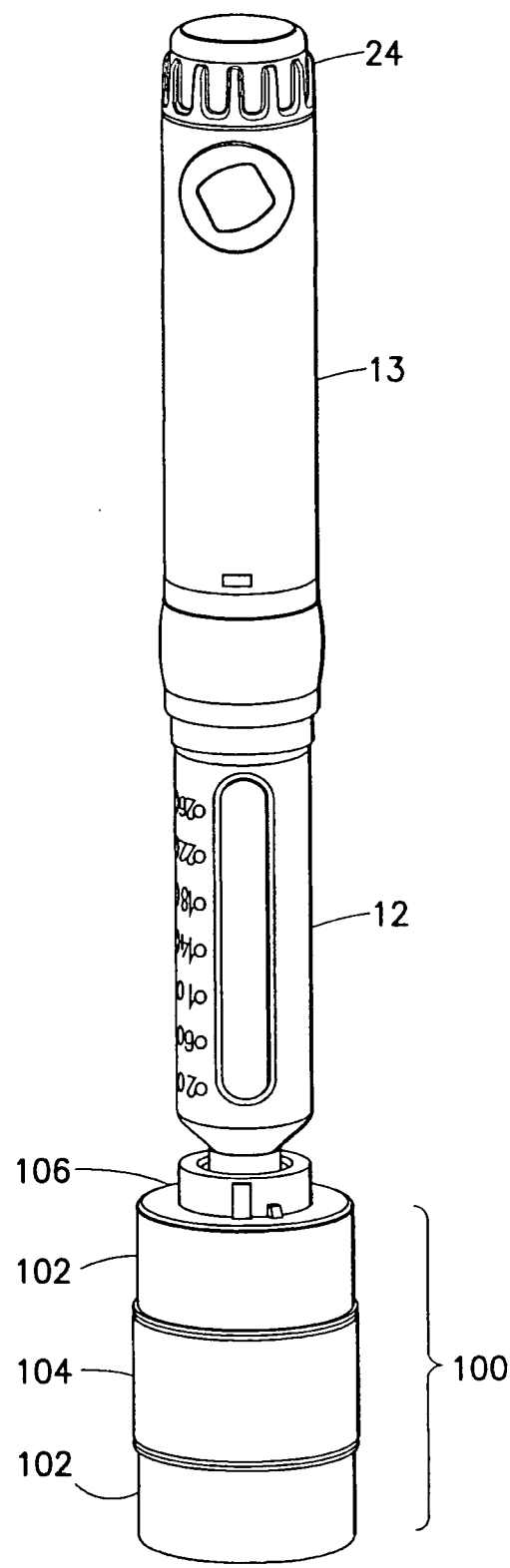
FIG. 3 is a perspective view of a ramp-type needle changing assembly provided with an exemplary drug delivery pen according to an exemplary embodiment of the present invention.

In an exemplary embodiment shown in FIG. 3, the system and method comprises an attachable needle storage device 100 provided with a main body 102 and a rotatable sleeve 104. In the exemplary embodiment shown, the main body 102 and sleeve 104 are cylindrical, but are not limited thereto. As described in greater detail below, the sleeve 104 is configured to rotate about the main body 102, and the main body and sleeve are configured to retract or slide together along an axial direction of the pen body 10. Further, at least one end of the main body 102 comprises a circular engagement feature 106 to releasably secure the attachable needle storage device 100 to the pen body 10, and in doing so, locate the septum of the medicament cartridge to be accessed by the new needles of the device 100.

Figure 2A:
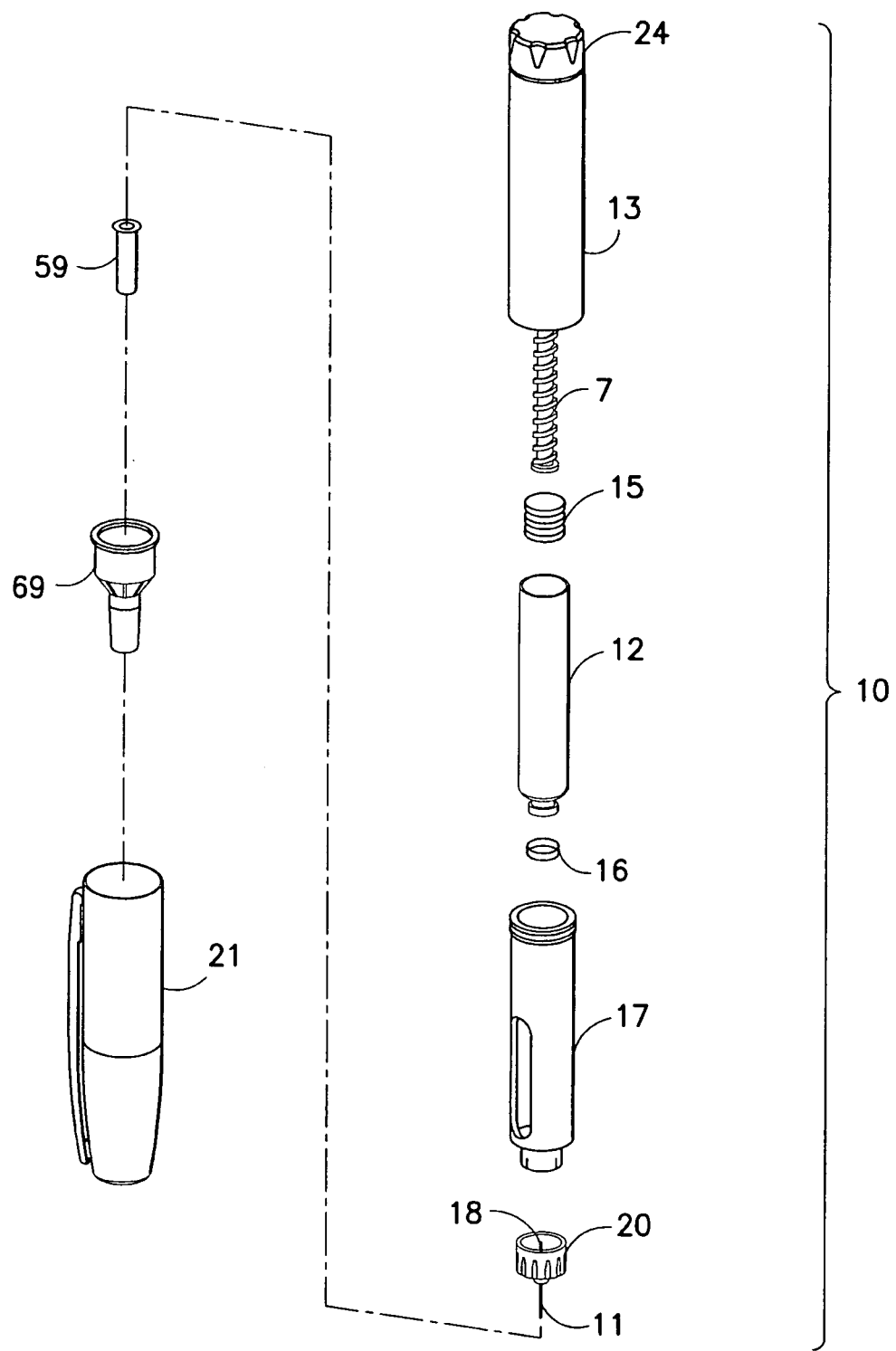
FIG. 2A is an exploded perspective view of the components of the drug delivery pen of FIG. 1.
Figure 2B:
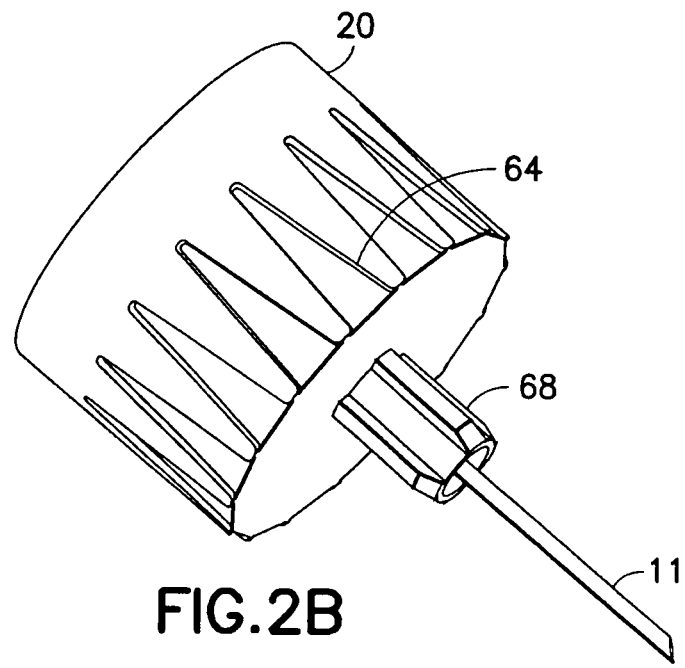
FIGS. 2B and 2C are enlarged perspective views of the pen needle for use with the drug delivery pen of FIG. 1.
Figure 2C:
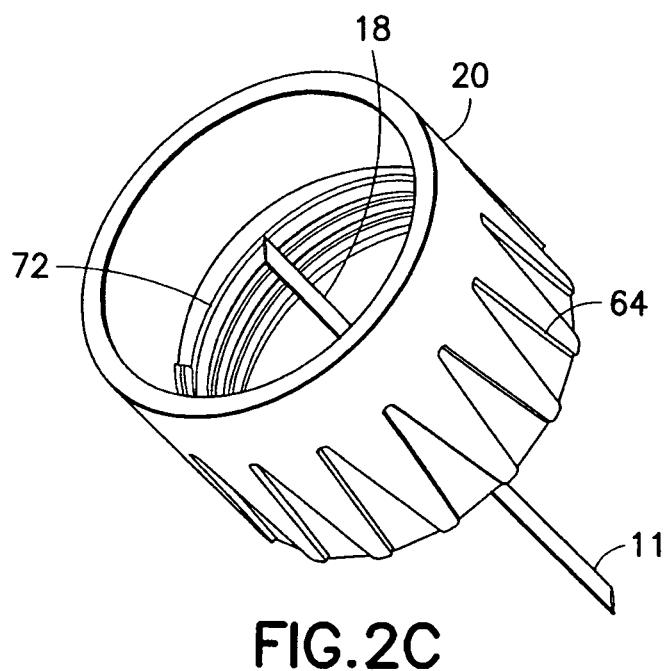
Figure 4:
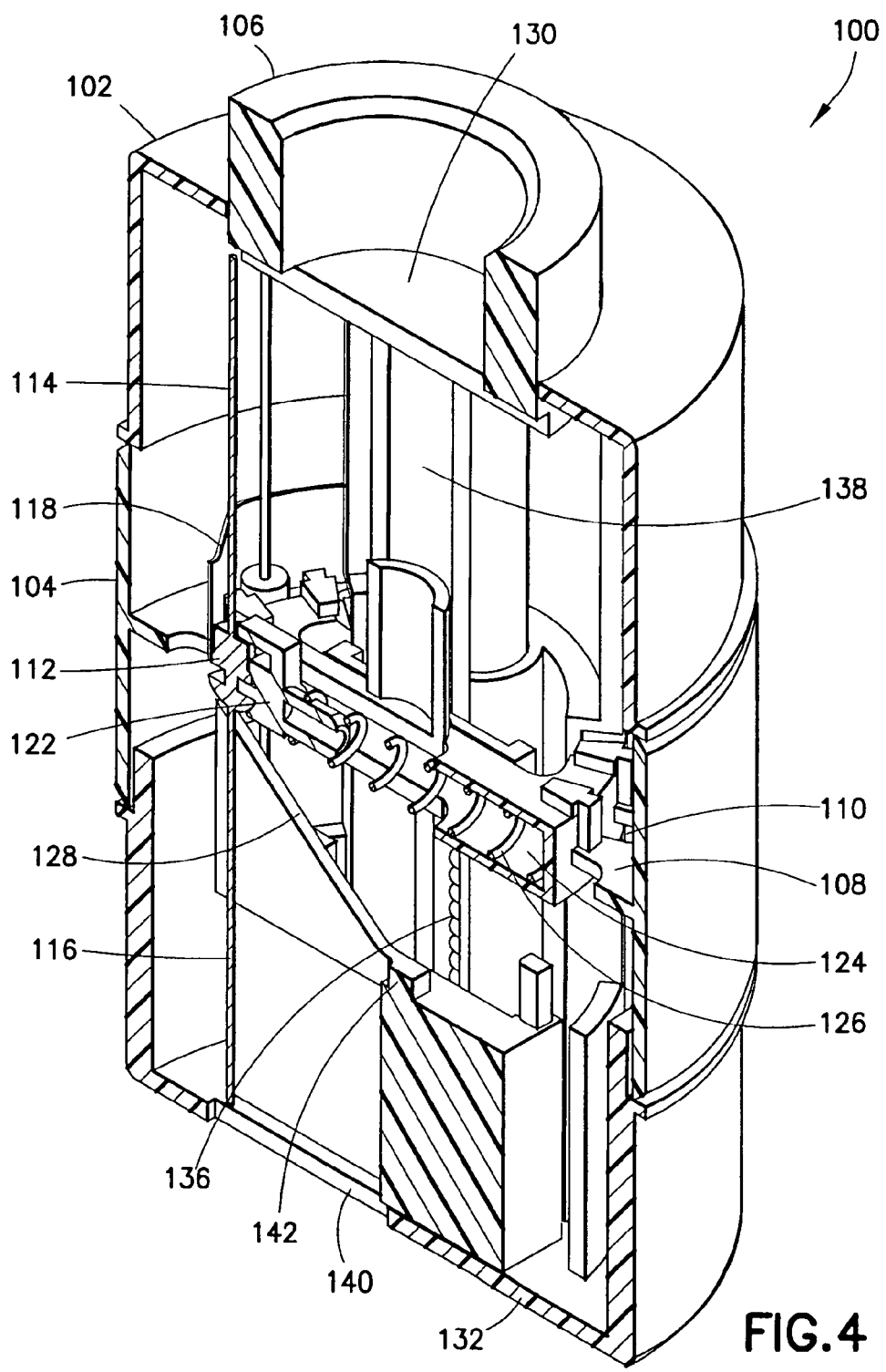
FIG. 4 is an enlarged sectional view of the ramp-type needle changing assembly of FIG. 3 according to an exemplary embodiment of the present invention.
Figure 5:
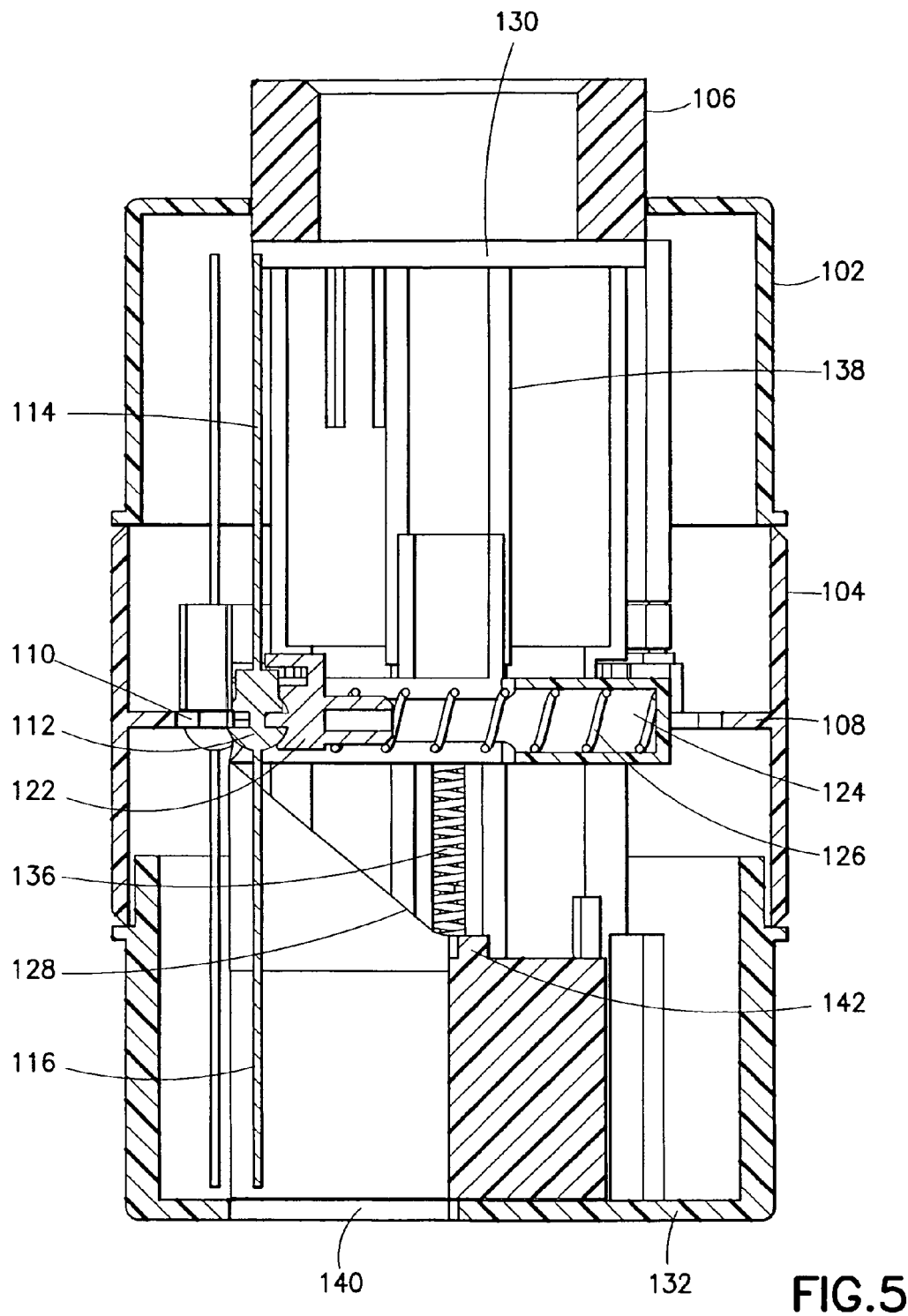
FIG. 5 is another enlarged sectional view of the ramp-type needle changing assembly of FIG. 3 according to an exemplary embodiment of the present invention.

As shown in greater detail in FIG. 4, the sleeve 104 is rotably captured between flanges of an upper and lower portion of the main body 102, and comprises a rotating tray 108. The rotating tray 108 comprises a plurality of slotted openings 110 in which a plurality of needles and needle hubs 112 can be releasably secured and entirely enclosed within the device. As noted above, FIGS. 2B and 2C are perspective views of the pen needle of FIG. 2A wherein the pen needle includes the hub 20, protrusion 68 and patient needle 11. The septum-penetrating needle cannula 18 disposed within the non-patient end of the hub 20 fluidly communicates with the patient needle 11, and the interior of the non-patient end of the hub 20 includes threads or other features 72 for connection with the pen injector. In these or other exemplary embodiments of the present invention the pen needle can omit one or more of the above features as long as sterility of both the patient and non-patient ends of the cannula is maintained. For example, an exemplary pen needle can be provided having a hub and cannula assembly only. Such an exemplary pen needle is described in the following embodiments, contained within the attachable needle storage device 100, which is configured to couple with the pen body 10 in place of a conventional needle hub.

Each of the needles 112 comprise a back end member 114 to pierce a septum of the medicament cartridge, a patient end member 116, and an intersection thereof where the slotted or contoured hub is provided for positioning in the slotted openings 110 of the tray 108. As shown in the exemplary embodiment, the entirety of the needle and associated needle hub 112 is enclosed within cavities of the upper and lower portions of the main body 102. That is, the attachable needle storage device 100 has a diameter slightly larger than the pen body 10, such that the extra space can be used to fully enclose and house the new needles until use and after use, fully enclose and house the used pen needles in the slotted openings of the rotating tray 108. In an exemplary embodiment, up to 25 needles can be stored in the attachable needle storage device 100, and wherein such needles comprise needles of between 26 and 34 gauge, but the invention is not limited thereto. In the exemplary embodiment shown, a single needle gauge is used for the plurality of needles. However, in other embodiments of the present invention, needles of different gauges can be used and identified by markings on the sleeve. Still further, one or more of the main body 102 and sleeve 104 can be colored or otherwise marked to indicate a needle size and type contained therein.

Figure 7A:
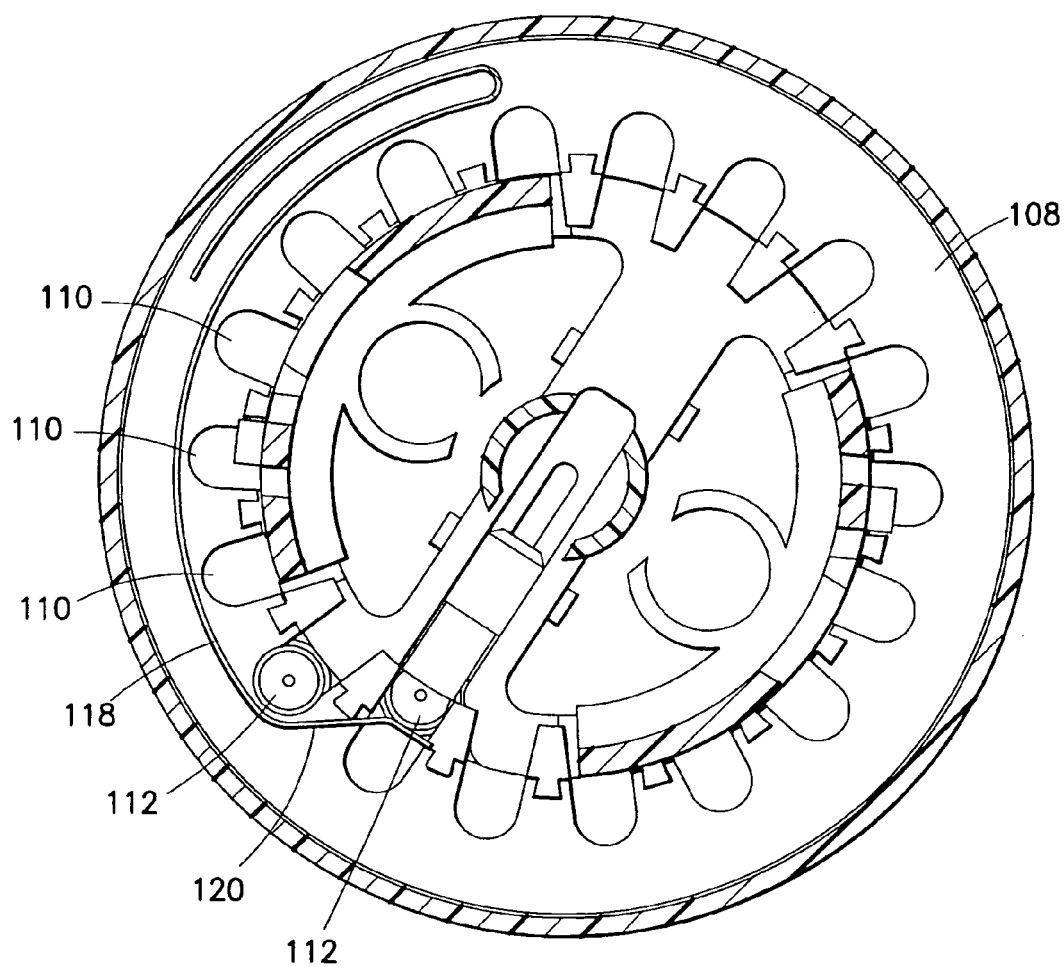
FIG. 7A is another enlarged sectional view of the ramp-type needle changing assembly of FIG. 3 illustrating an exemplary leaf spring according to an exemplary embodiment of the present invention.
Figure 7B:
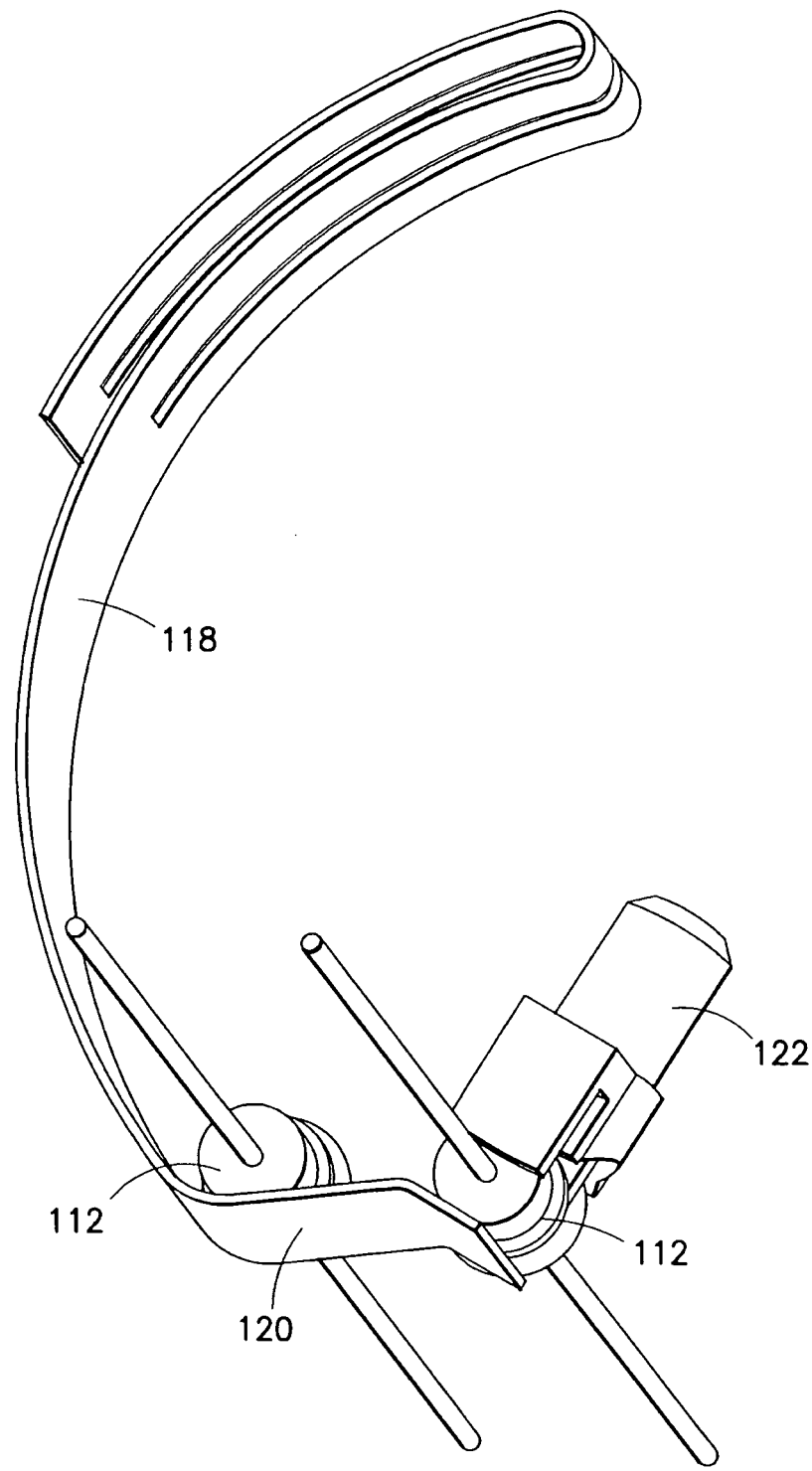
FIG. 7B is an enlarged view of the exemplary leaf spring of FIG. 7A according to an exemplary embodiment of the present invention.

To move the needles to and from the rotating tray 108, a leaf spring is provided to urge new needles from the tray and onto a shuttle, and a return spring, shuttle and needle tray are provided to return used needles to the tray. As shown in FIGS. 4 and 7A and 7B, the leaf spring 118 is secured in the opening provided by the upper portion of the main body 102 to direct each needle, at a specific rotational point, from the rotating tray 108 when rotated. That is, the leaf spring 118 is secured to the upper portion of the main body 102 such that an inclined end 120 thereof is contacted by the needle and needle hub 112 when rotated to that point, and the inclined end 120 directs the needle and needle hub 112 from the tray 108 and onto the shuttle 122 to then be moved to the axial position of the pen body 10 as described in greater detail below.

To receive the needle and needle hub 112 at the axial position of the pen body 10, the main body 102 provides the shuttle 122 at a point adjacent to a slotted opening of the slotted openings 110 of the rotating tray 108. Accordingly, as the sleeve 104 and tray 108 are rotated and a needle and needle hub 112 contact the inclined end 120 of the leaf spring 118, the needle and needle hub 112 are moved from the slotted opening of the tray 108 and onto the shuttle 122. Prior to this, as the user turns the sleeve, the new needle being transferred to the shuttle deflects the inclined end 120 of the leaf spring 118 and at this point, without the counter force provided by the inclined end 120 of the leaf spring 118, the shuttle, under return spring 126 force itself, first expels a used needle onto an opening 110 of the rotating tray 108 before receiving the new needle.

The shuttle 122 itself is configured to travel in a direction to and from a center axis of the device via an opening 124 as resisted by the return spring 126. In an exemplary embodiment of the present invention, there is a desired balance which exists between the leaf spring 118 and the shuttle return spring 126. The leaf spring 118 preferably must be stronger than the shuttle return spring 126, but yet allow low torque needle advancement. Once moved to the shuttle 122, the needle and needle hub 112 can then be moved to the center axis of the device and once in such a center position, posts on the ramp unsnap a needle tray such that the shuttle 122, needle and needle hub 112, and needle tray 124 are moved rearward as pulled engaging the septum and exposing the distal end of the needle for injection.

Figure 6:
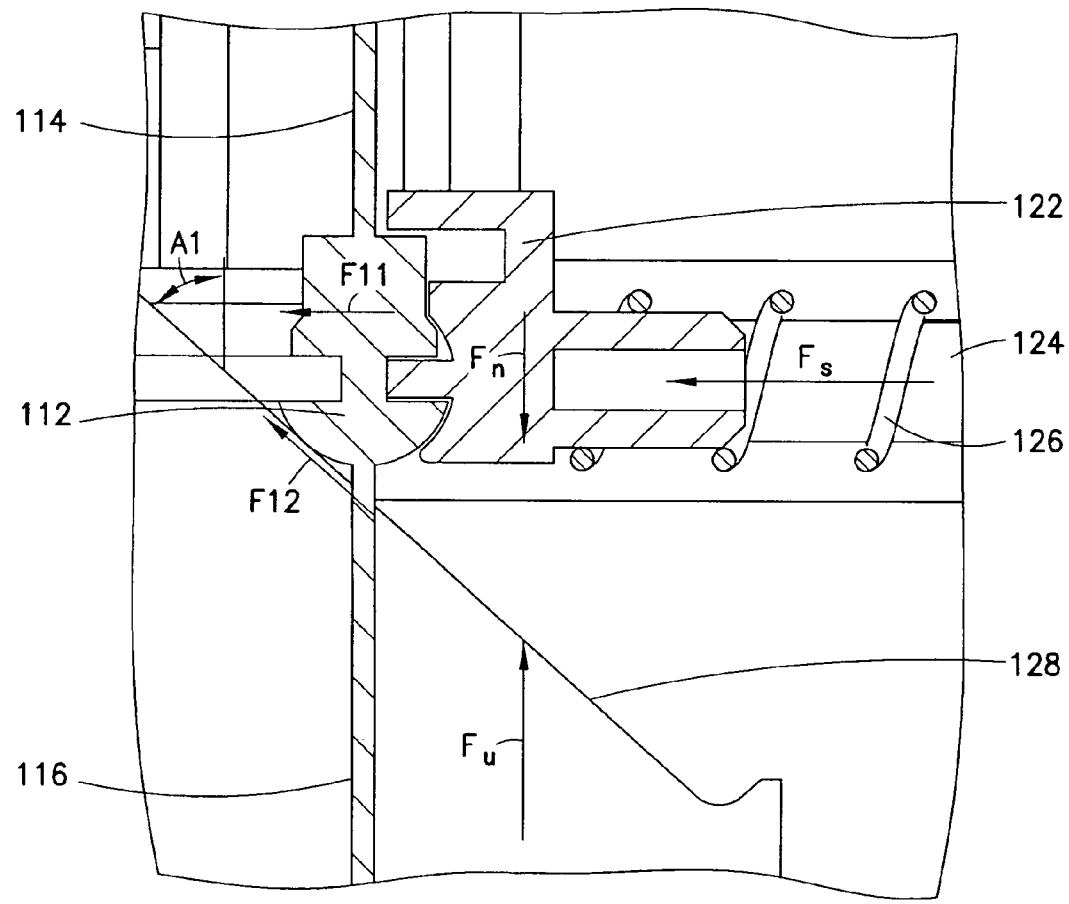
FIG. 6 is another enlarged sectional view of the ramp-type needle changing assembly of FIG. 3 illustrating exemplary force vectors according to an exemplary embodiment of the present invention.

To do so, the lower portion of the main body 102 comprises the ramp 128 which can be retracted or pulled rearward with the main body 102 and sleeve 104 while the shuttle 122 is prevented from moving rearward with the body and sleeve through contact with an end of the medicament cartridge, such that the rearward moving ramp 128 engages the shuttle 122 at some point and moves the shuttle 122 and the needle and needle hub 112 contained therein, into an axial position of the pen body. Specifically, the shuttle 122 is engaged with the ramp 128 when the user retract or pulls rearward on the device and the ramp 128 contacts the hub of the needle and needle hub 112. The exemplary ramp 128 shown in FIGS. 4 and 6 is configured to have an approximately 45° inclined contact surface, but is not limited thereto, such that the ramp translates 1 mm of vertical movement into 1 mm of horizontal movement, transferring the shuttle 122 and needle away from the rotating tray 108 toward the axial or delivery position, underneath a septum of a medicament cartridge.

Once the shuttle 122 is in the axial or delivery position, the engagement feature 106 and opening passageway 138 remain fixed. The horizontal opening passageway or needle tray 124 is passively snapped to the vertical opening passageway 138, so that it can be released by the ramp 128. That is, the horizontal opening passageway or needle tray 124 is passively snapped to the vertical opening passageway 138 to allow the ramp 128 to engage the shuttle 122 and move the shuttle 122 and the needle and needle hub 112 contained therein, into an axial position of the pen body. While doing so, the horizontal opening passageway or needle tray 124 snapped to the vertical opening passageway 138 remain stationary, while the device and ramp 128 are pulled rearward, and the rearward motion is translated into movement of the shuttle 122 and the needle and needle hub 112 contained therein into an axial position of the pen body along the needle tray 124. Once in position, rearward movement of the shuttle 122, needle and needle hub 112, and needle tray 124 is desired which requires that the needle tray 124 be released from the vertical opening passageway 138. To do so, the ramp 128 is provided with features to release the needle tray 124 from the vertical opening passageway 138.

For example, once the shuttle 122 reaches the bottom of the ramp 142, posts 144 and 146 of the ramp 128 release passive snaps 152 between the needle tray 124 and the vertical opening passageway 138, allowing the shuttle 122, needle and needle hub 112, and needle tray 124 to be pulled upward and driving the needle through the septum. To do so, the vertical opening passageway 138 comprises at least one projection or detent of the passive snaps 152 that is configured to secure the needle tray 124 to the vertical opening passageway 138.

Once the needle and needle hub 112 is under the septum, the user can continue pulling on the device, such that the shuttle 122, needle and needle hub 112, and needle tray 124 are pulled rearward in one or more slots 154 of the vertical opening passageway 138 and the back end member 114 of the needle pierces the septum, and the patient end member 116 of the needle is exposed for use. The main body 102 and sleeve 104 are held in the retracted position by a separate projection or inclined detent 184 on the opening passageway 138, against the urging of the spring 136, until released. When pulled rearward, a detent 186 of the main body 102 and sleeve 104 engage and deflect the inclined detent 184 of the on the opening passageway 138 to thereby hold the main body 102 and sleeve 104 in the retracted position for use. As described in greater detail below, the inclined detent 184 is configured to be releasably deflected by the placement of a shield on the distal end of the device.

In an exemplary embodiment of the present invention, one or more of the ends 114 and 116 of the needle comprise sterility barriers (not shown), that are slid over or otherwise cover the portions of the needles which pierce the septum and/or the patient, such that each needle is individually sterile. Exemplary embodiments of such sterility barriers covering the needle ends can be comprised of septum-like rubber materials (i.e., coatings), but are not limited thereto. The needle ends are configured to pass through the ends 130 and 132 of the device, which can be provided with openings or also made of a pierceable material. For example, the end 132 of the lower portion of the main body 102 is provided with a slot opening 140 to provide clearance for the patient end 116 of the needle 112 necessary as the main body portion 102 is retracted rearward and the shuttle 122 is moved. The opening is preferably configured as a slot 140 as the projecting needle is moving toward the axis as the main body portion 102 is retracted rearward.

During engagement with the ramp 128, the shuttle 122 is moved through the needle tray 124 to the axial position and in doing so, compresses the return spring 126. Accordingly, when the device is pulled forward in the opposite direction, the spring 126 urges the shuttle 122 in the reverse direction. Further, as the main body 102 and sleeve 104 are pulled rearward, the spring 136 is compressed. Once the shuttle 122 reaches the bottom of the ramp 142, posts 144 and 146 of the ramp 128 release passive snaps 152 between the needle tray 124 and the vertical opening passageway 138, allowing the shuttle 122, needle and needle hub 112, and needle tray 124 to be pulled upward and driving the needle through the septum. The vertical opening passageway 138 comprises at least one projection or detent of the passive snaps 152 that is configured to secure the needle tray 124 to the vertical opening passageway 138, and is configured to be released by the posts 144 and 146 of the ramp 128.

As noted above, at least one end of the main body 102 comprises a circular engagement feature 106 to releasably secure the attachable needle storage device 100 to the pen body 10, and in doing so, locate the septum of the medicament cartridge to be accessed by the new needles of the device 100. Any number of connection means can be used including a press fit, threaded fit, or luer or luer lock mechanism. Accordingly, a pierceable septum of a medicament cartridge 12 can be positioned in the opening of the engagement feature 106, against the end 130 to be pierced by the back end member 114 of the needle when the device is pulled rearward by the user.

The engagement feature 106 is configured to remain stationary upon the end of the pen body 10, as the main body 102 and a rotatable sleeve 104 of the device 100 can be retracted or pulled rearward over the end of the pen body 10. The engagement feature 106 further comprises the vertical opening passageway 138 extending therefrom, and intersecting the needle tray 124 in which the shuttle 122 travels and which prevents rearward movement of the shuttle 122 until alignment with the opening passageway 138 and the pen body 10, and engagement with the ramp 128. Once in alignment with the opening passageway 138 and the pen body 10, and after release by the ramp posts 144 and 146, the shuttle 122, needle and needle hub 112, and needle tray 124 can be pulled rearward sufficiently to pierce the septum of the medicament cartridge.

As also noted above, the device is secured in this position for use by at least one detent against a compressed spring and after use, a needle shield is used to unlock the detent and the compressed spring, which is configured to pull the needle from the septum, and return the device to the transport state, where the previous steps can be repeated. The shuttle 122, needle and needle hub 112, and needle tray 124 are urged back into the distal position by the spring 136. As the shield moves into the device, it unlocks the spring 136 which was compressed during the needle attachment. The spring 136 then releases the device to move back toward the distal end of the pen, and the shuttle 122 of the device has arms which pull the needle from the pen septum. The spring 126 then urges the shuttle 122 in the reverse direction and when the sleeve is turned to install a new needle, the used needle is returned to the disc upon deflection of the leaf spring.

In the exemplary embodiments of the present invention described above, the automatic release step could be replaced by a manual reset step. For example, instead of the shield triggered spring 136 pulling the needle from the septum after delivery, the user could simply slide the device in the distal direction, manually pulling the needle from the septum after delivery and resetting the system.

As shown in FIG. 6, the static forces required to manipulate the needle with an inclined plane such as that provided by the ramp 128 are as follows.

$$Fu = \frac{Fs \cdot \sin(A1) \cdot \sin\left(\frac{\pi}{2} - A1\right)}{1 - \mu\left(\sin(A1) \cdot \sin\left(\frac{\pi}{2} - A1\right) + \cos(A1) \cdot \sin(A1) \cdot \sin\left(\frac{\pi}{2} - A1\right)\right)}$$

In the above equation, Fu is the force vector moving the ramp upward, Fs is the force vector of the spring 126, A1 is the angle between the incline of the ramp and the direction of force vector Fu, and µ is the coefficient of friction, which is an empirical property of the contacting materials. The force vector Fs of the spring opposing the movement of the shuttle 122 is overcome by the force vector Fu moving the ramp 128 upward. That is, with the angle of the ramp A1 shown, the force vectors F11 and F12 overcome the normal force vector Fn and the spring force vector Fs to move the shuttle toward the axial center of the pen body. Further, the travel of the needle and needle hub 112 is restricted to movement only toward the axial center of the pen body until reaching the axial center of the pen body, and upon reaching the opening passageway 138, rearward movement is permitted.

Accordingly, as the user rotates the sleeve 104, a new needle and needle hub 112 is forced onto the shuttle 122 through contact with the leaf spring 118 after the used needle is moved from the shuttle 122 to an open slot or fork 110 in the annular component tray 108. To facilitate the transfer from the storage slots or forks 110 to the shuttle 122, the leaf spring 118 remains in contact with the needle hubs as they are rotated past. As the user turns the sleeve 104, the new needle 112 being transferred to the shuttle 122 deflects the leaf spring 118. Without the counter force provided by this leaf spring 118, the shuttle 122, under spring 126 force itself, first expels the used needle onto a slot or fork 110 on the annular component tray 108.

Once a new needle 112 is placed on the shuttle 122, the user then retracts or pulls the device 100 proximally up the pen body 10. This vertical motion causes the ramp 128 within the device 100 to engage the needle and needle hub 112 now in the shuttle 122, moving it horizontally toward the axial position of the pen body 10 and in alignment with a septum of a medicament cartridge. Once under the septum, the user continues pulling the device 100 vertically, posts on the ramp unsnap a needle tray such that the shuttle 122, needle and needle hub 112, and needle tray 124 are moved rearward in the opening passageway 138 and the back end 114 of the needle 112 engages the septum and a patient end 116 of the needle 112 becomes exposed at the distal end of the device 100 for injection. The device is releasably locked in this position by the engagement of the detents 184 and 186 against the compressed spring 136. After use, the needle shield is used to release the detents 184 and 186 such that the spring 136 pulls the needle and needle hub 112 from the septum, and returns the device 100 to the transport state, where the previous use steps can be repeated.

Exemplary embodiments of the present invention can integrate the needle changing process into a single device, wherein the new and used needles are not exposed during the change or storage, and simply a distal end of the new needle becomes gradually exposed in the final stages of change.

Needle storage, attachment, removal, and disposal can be accomplished via a simple turning and pulling motion of a single system, wherein the stored needles are not exposed and located around the perimeter of the device, fixed via slots or forks into the rotatable tray. When the user turns the tray or sleeve, new needles are fed onto the spring loaded shuttle, and used needles are ejected from the shuttle. The shuttle is then engaged when the user pulls on the device as the ramp contacts the needle and needle hub to load the new needle. Likewise, when the user installs the shield, the used needle is unloaded and stored in a position previously occupied by the new needle.

Figure 8:
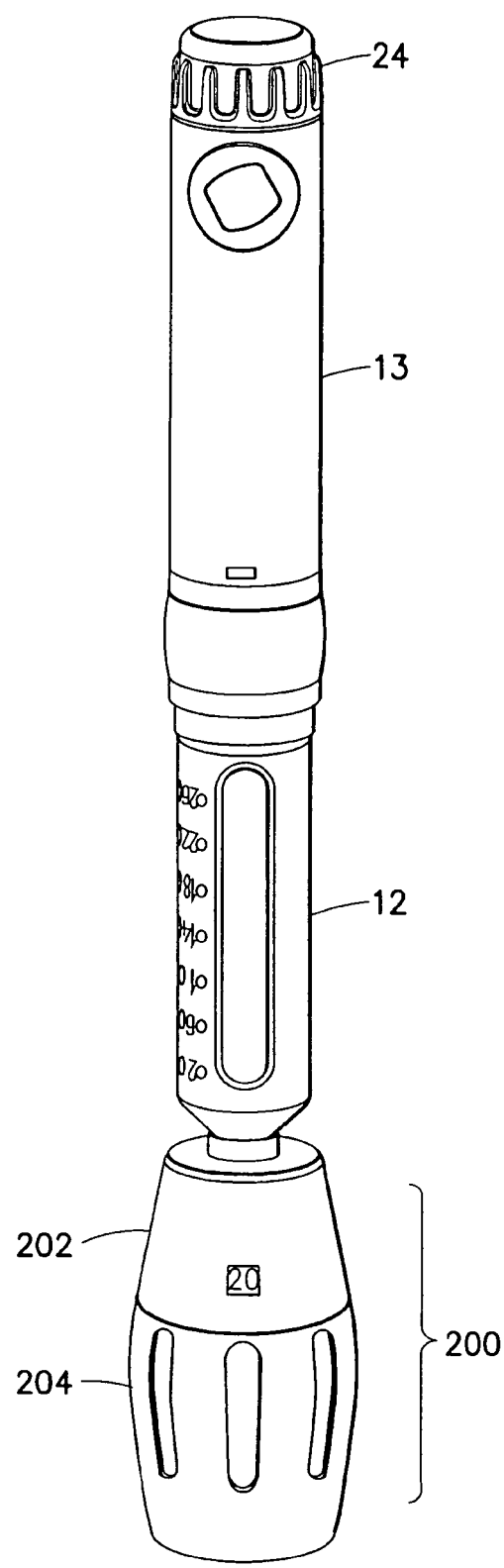
FIG. 8 is a perspective view of a ramp-type needle changing assembly provided with an exemplary drug delivery pen according to another exemplary embodiment of the present invention.

In yet another exemplary embodiment of the present invention shown in FIG. 8, the attachable needle storage device 200 can be provided substantially as described above, but having only an upper portion of a main body 202 and a lower portion comprising the rotatable sleeve 204. In such an exemplary embodiment, the contours can be configured to provide a seamless outer device surface for even greater ease of use for a user.

Figure 9A:
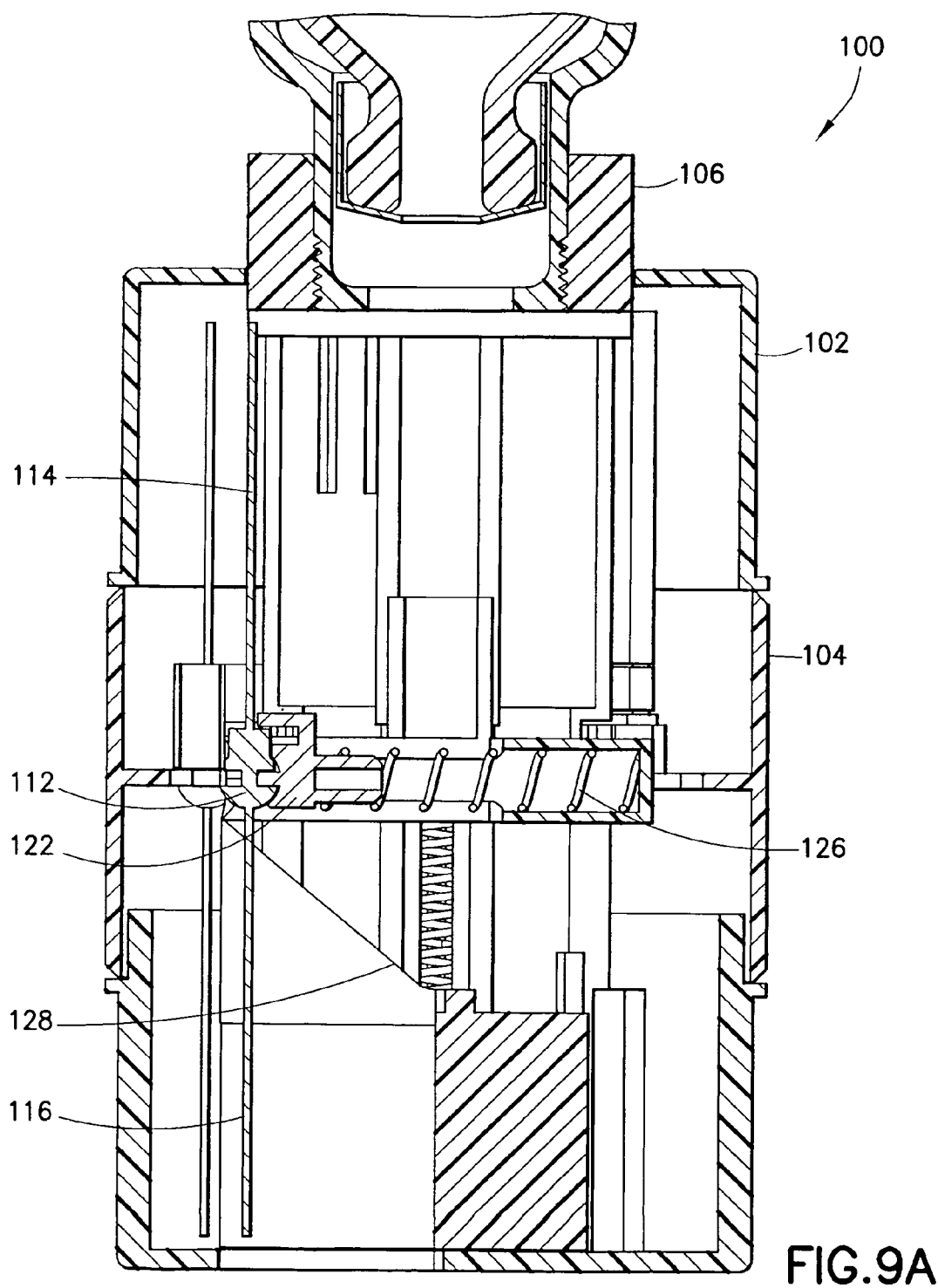
FIGS. 9A-9E are enlarged sectional views of the ramp-type needle changing assembly of FIG. 3 illustrating use stages according to an exemplary embodiment of the present invention.

FIGS. 9A-9E are enlarged sectional views of the ramp-type needle changing assembly of FIG. 3 illustrating stages of use according to an exemplary embodiment of the present invention. FIG. 9A shows a start position. As noted above, as the sleeve 104 and tray 108 are rotated and a needle and needle hub 112 contact the inclined end 120 of the leaf spring 118, the needle and needle hub 112 are moved from the slotted opening of the tray 108 and onto the shuttle 122. As the user turns the sleeve, the needle being transferred to the shuttle deflects the inclined end 120 of the leaf spring 118 and at this point, without the counter force provided by the inclined end 120 of the leaf spring 118, the shuttle, under return spring 126 force itself, first expels a used needle onto an opening 110 of the rotating tray 108 before receiving the new needle.

Figure 9B:
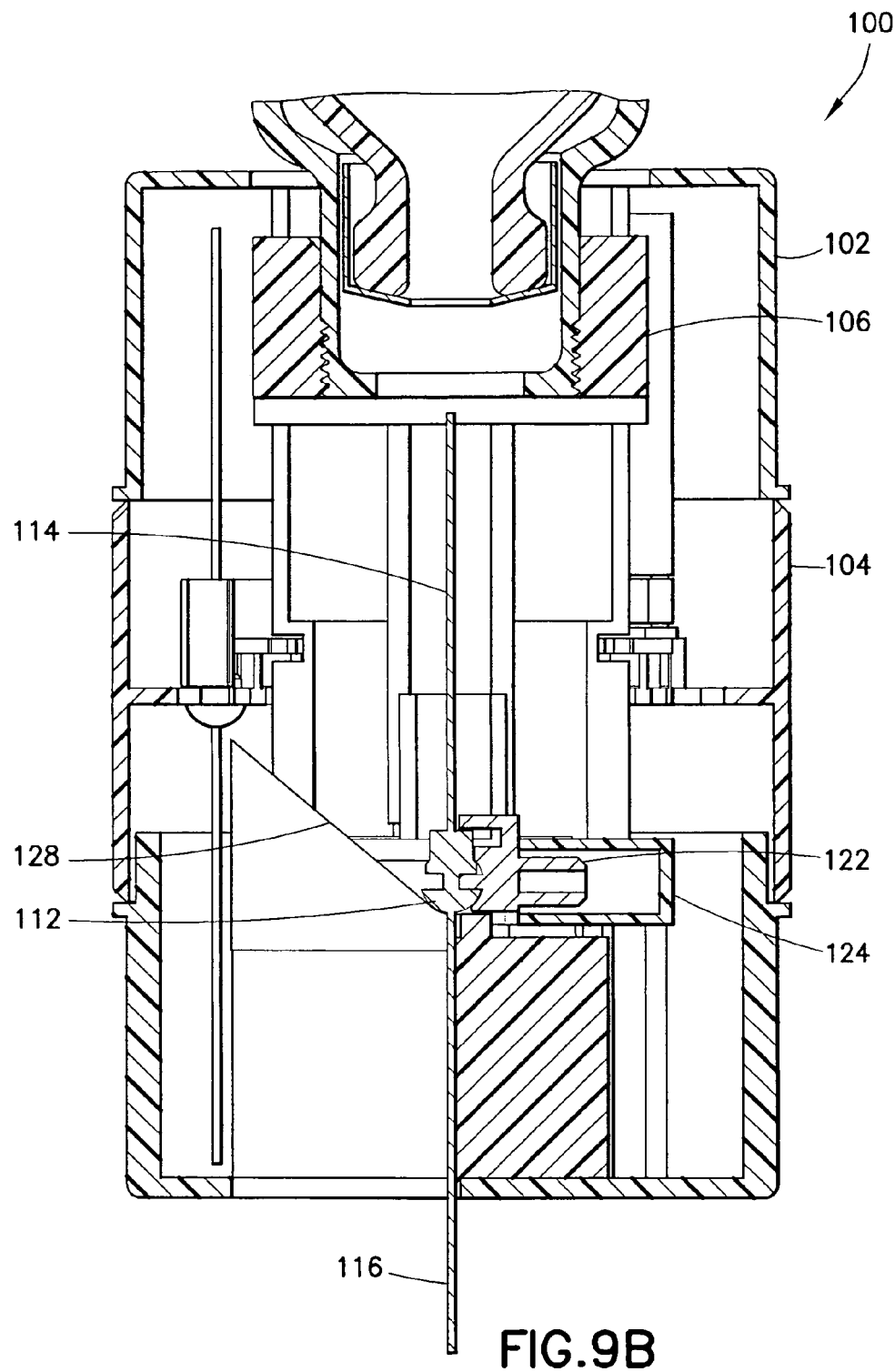

FIG. 9B shows a position after ramp engagement to the point where the shuttle 122 has been moved to a center or axial position beneath the septum. As noted above, once moved to the shuttle 122, the needle and needle hub 112 are then moved to the center axis of the device by ramp engagement and once in such a center position, posts on the ramp 128 release the needle tray 124 such that the shuttle 122, needle and needle hub 112, and needle tray 124 can be retracted rearward to pierce a septum of the medicament cartridge and expose a patient needle end at a distal end. The lower portion of the main body 102 comprises the ramp 128 which can be retracted or pulled rearward with the main body 102 and sleeve 104 while the needle tray 124 and opening passageway 138 are prevented from moving rearward with the body and sleeve through contact with an end of the medicament cartridge, such that the rearward moving ramp 128 engages the shuttle 122 and moves the shuttle 122 and the needle and needle hub 112 contained therein, into an axial position of the pen body as shown in FIG. 9B. Specifically, the shuttle 122 is engaged with the ramp 128 when the user retract or pulls rearward on the device and the ramp 128 contacts the hub of the needle and needle hub 112 which travel along the incline of the ramp to be displaced to the center or axial position.

Figure 9C:
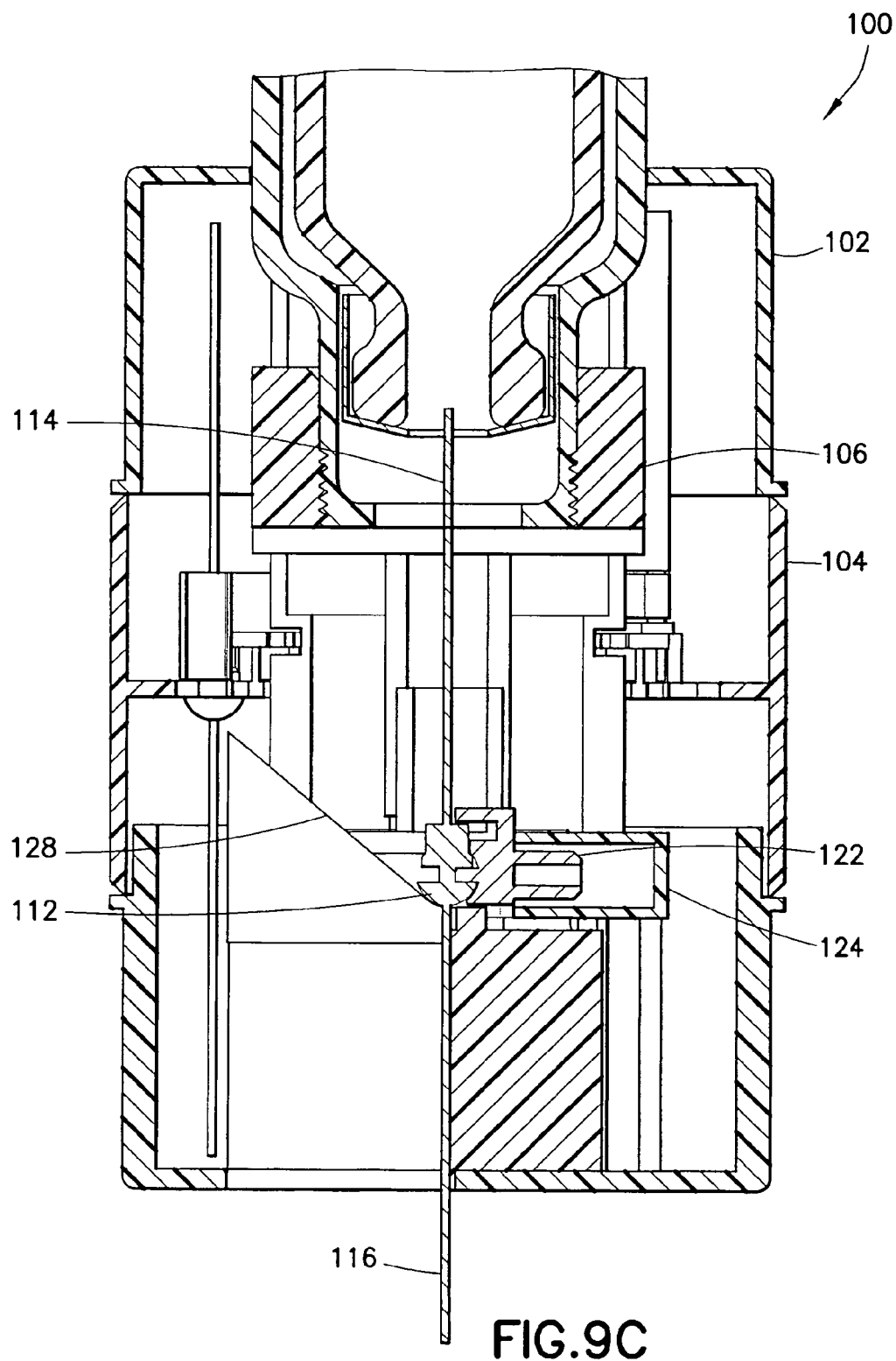
Figure 9D:
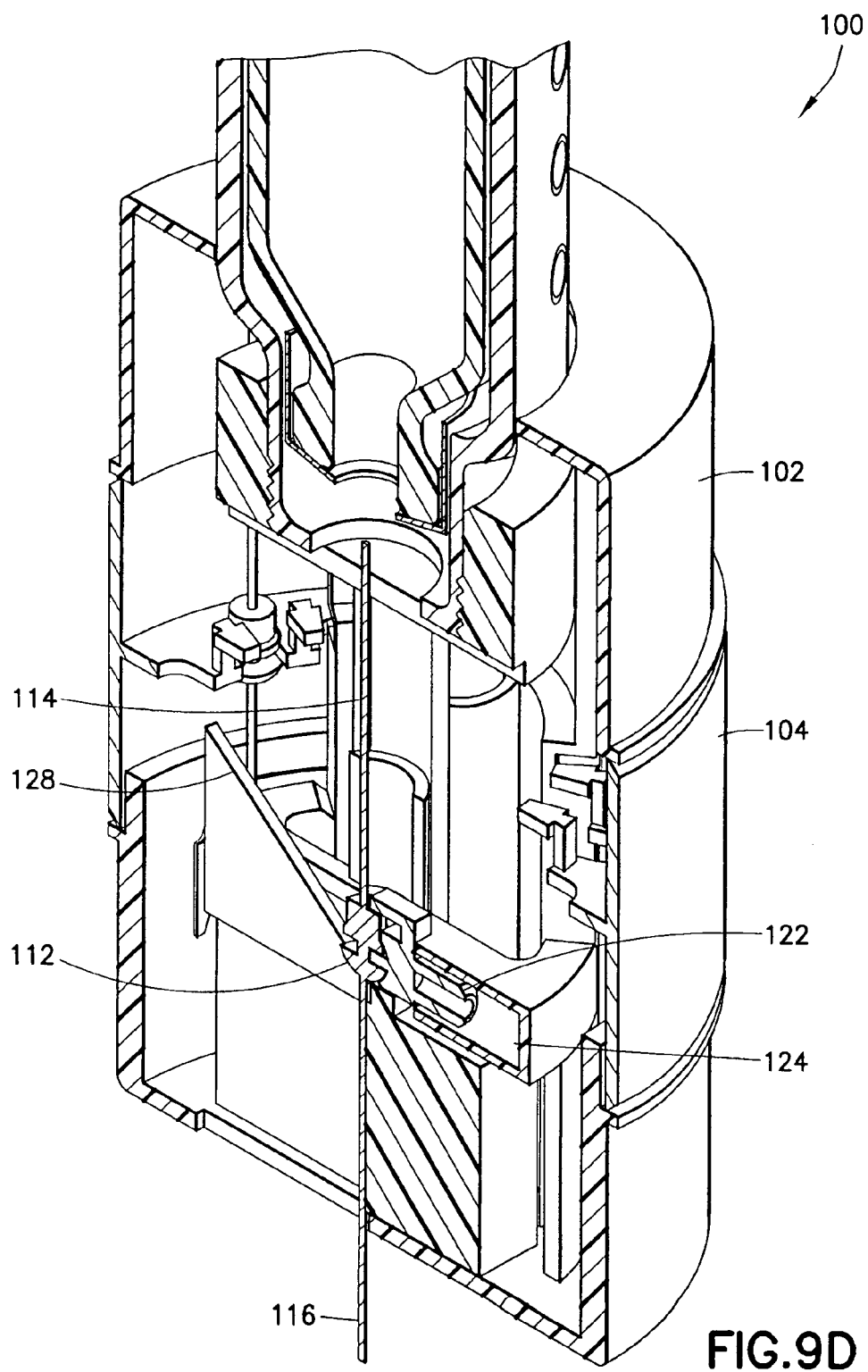

FIGS. 9C and 9D are views showing a position after ramp engagement and further rearward travel to the point where the shuttle 122, needle and needle hub 112, and needle tray 124 have been moved rearward and the needle pierces the septum. As noted above, once the shuttle 122 is in the center position, only the engagement feature 106 and opening passageway 138 remain fixed. The needle tray 124 is passively snapped to the vertical opening passageway 138 so that it can be released by posts of the ramp 128. For example, once the shuttle 122 reaches the bottom of the ramp 142, posts 144 and 146 of the ramp release the passive snaps between the needle tray 124 and the vertical opening passageway 138, allowing the shuttle 122, needle and needle hub 112, and needle tray 124 to be pulled upward and driving the needle through the septum.

Figure 9E:
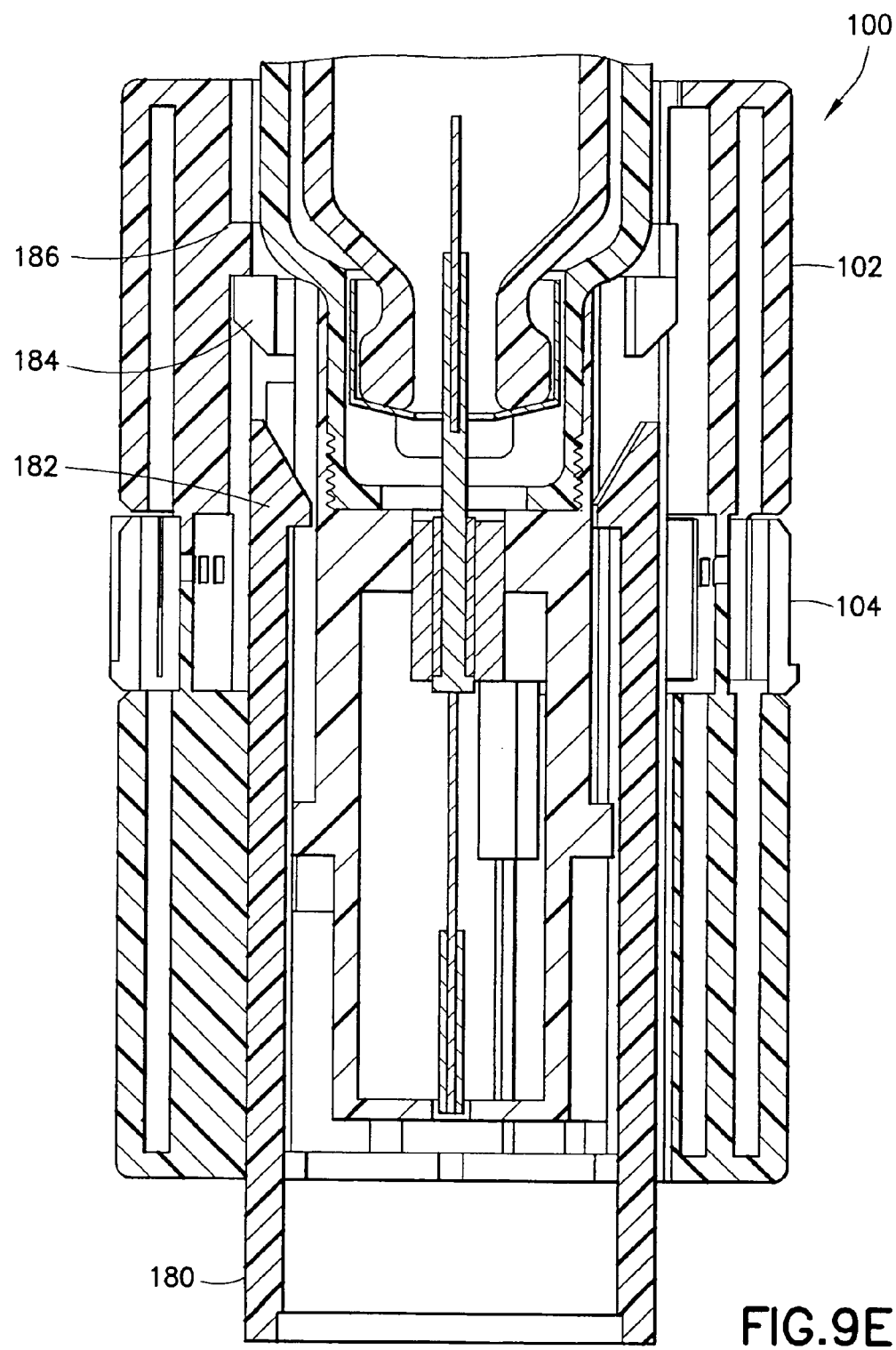

When pulled upward, a detent 186 of the main body 102 and sleeve 104 engage and deflect the inclined detent 184 of the on the opening passageway 138 to thereby hold the main body 102 and sleeve 104 in the retracted position for use. As described in greater detail below, the inclined detent 184 is configured to be releasably deflected by the placement of a shield on the distal end of the device. FIG. 9E shows a position where a shield 180 is being installed and a detent 182 of the shield is approaching the inclined detent 184 of the device holding the main body 102 and sleeve 104 in the retracted position against the urging of the spring 136, until released. The spring 136 then releases the device to move back toward the distal end of the pen, and the shuttle 122 of the device uses the arms securing the hub of the needle to pull the needle from the pen septum. After the needle is pulled from the septum, the spring-loaded shuttle 122 returns the needle back to the perimeter of the device. In all other aspects, the attachable needle storage device 100 is configured to serve the functions otherwise associated with a conventional needle hub, such as skin contact functions. After use, a shield or other manual activation is used to reset the attachable needle storage device 100.

Figure 11B:
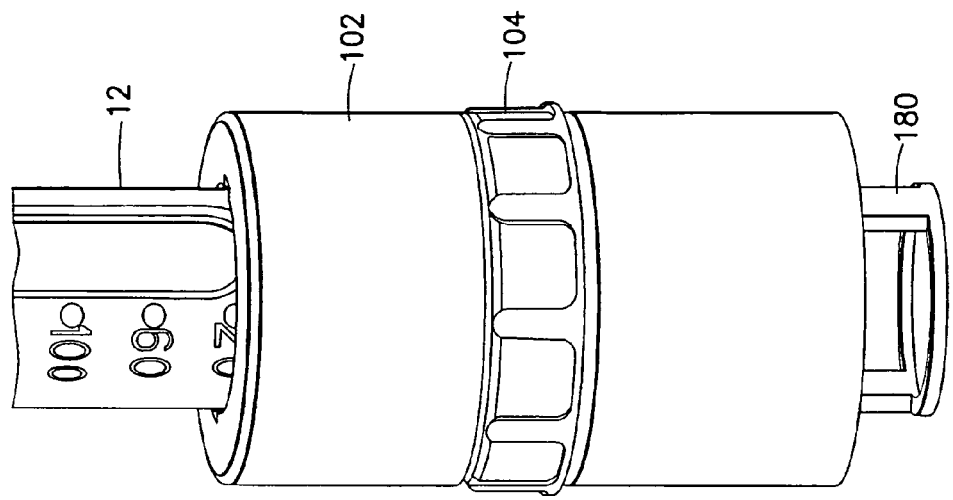
FIGS. 11A and 11B are enlarged perspective views of an exemplary shield unlock mechanism of the ramp-type needle changing assembly of FIG. 3 according to an exemplary embodiment of the present invention.
Figure 11A:
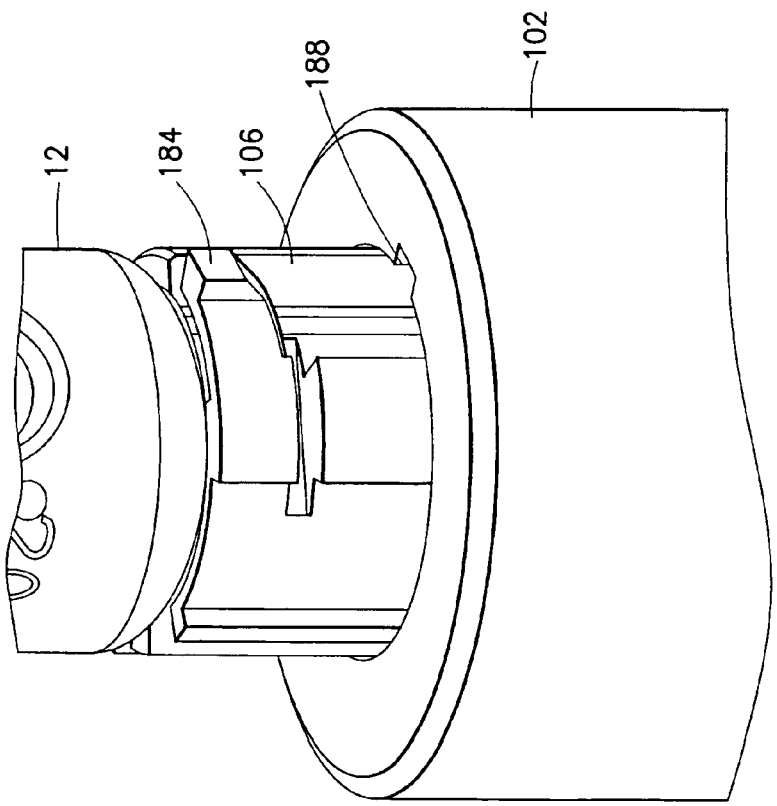

FIGS. 11A and 11B are enlarged perspective views of an exemplary shield in a pre-engaged position in FIG. 11A and a secured position in FIG. 11B. As shown in FIG. 11A, the inclined detent 184 is aligned with an opening 188 in the main body 102 to permit retraction of the main body 102. Once in the retracted position as described above and shown in FIG. 11B, the shield 180 can be installed an function to release the device as described above.

Figure 10A:
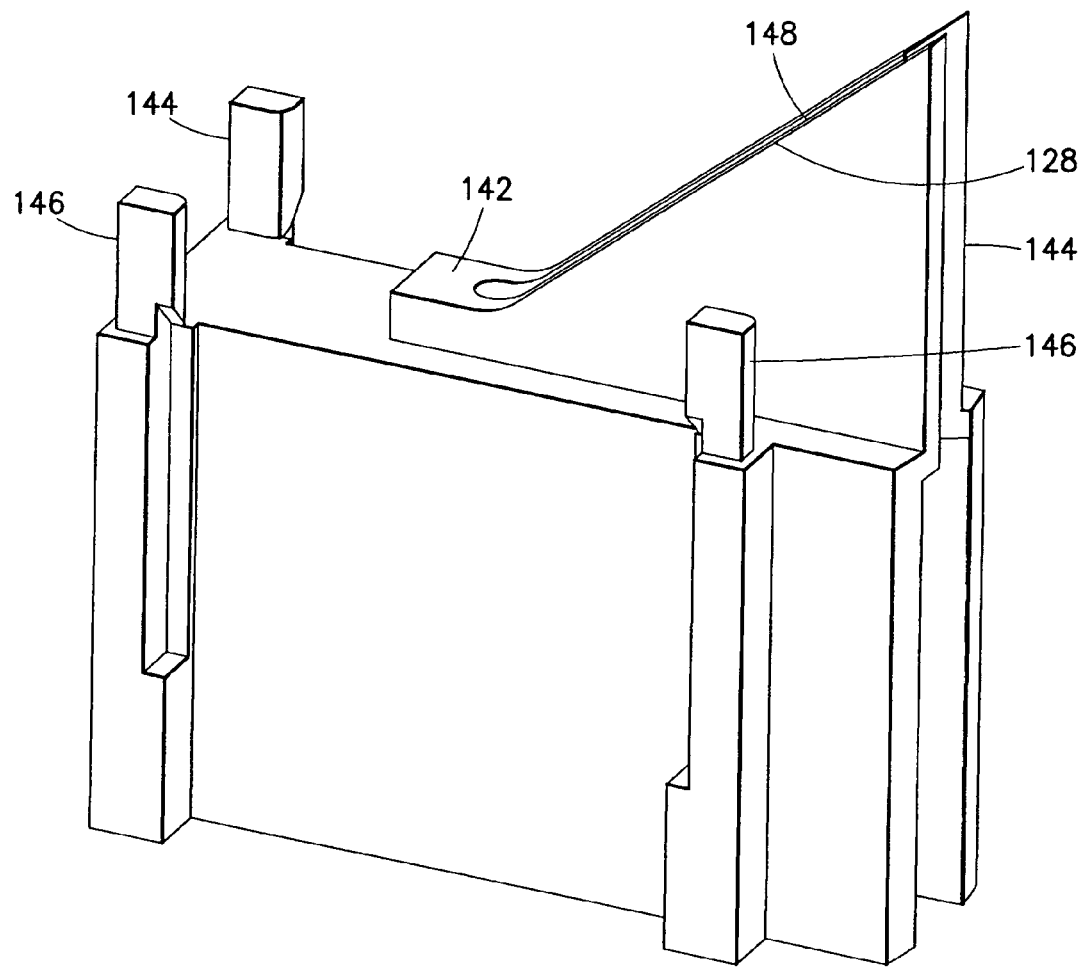
FIGS. 10A-10D are enlarged perspective views of an exemplary ramp and ramp engagement of the ramp-type needle changing assembly of FIG. 3 illustrating use stages of the ramp according to an exemplary embodiment of the present invention.
Figure 10B:
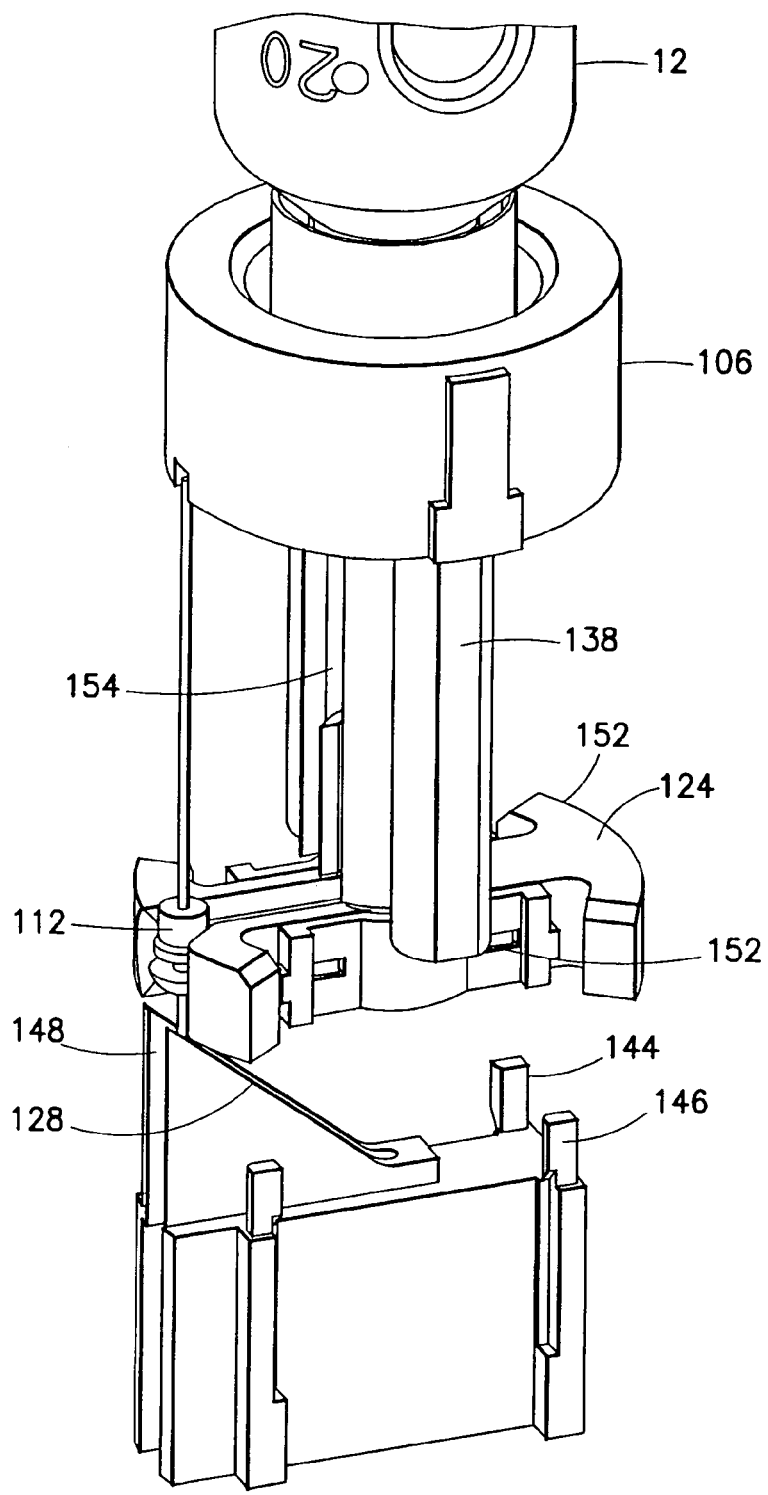
Figure 10C:
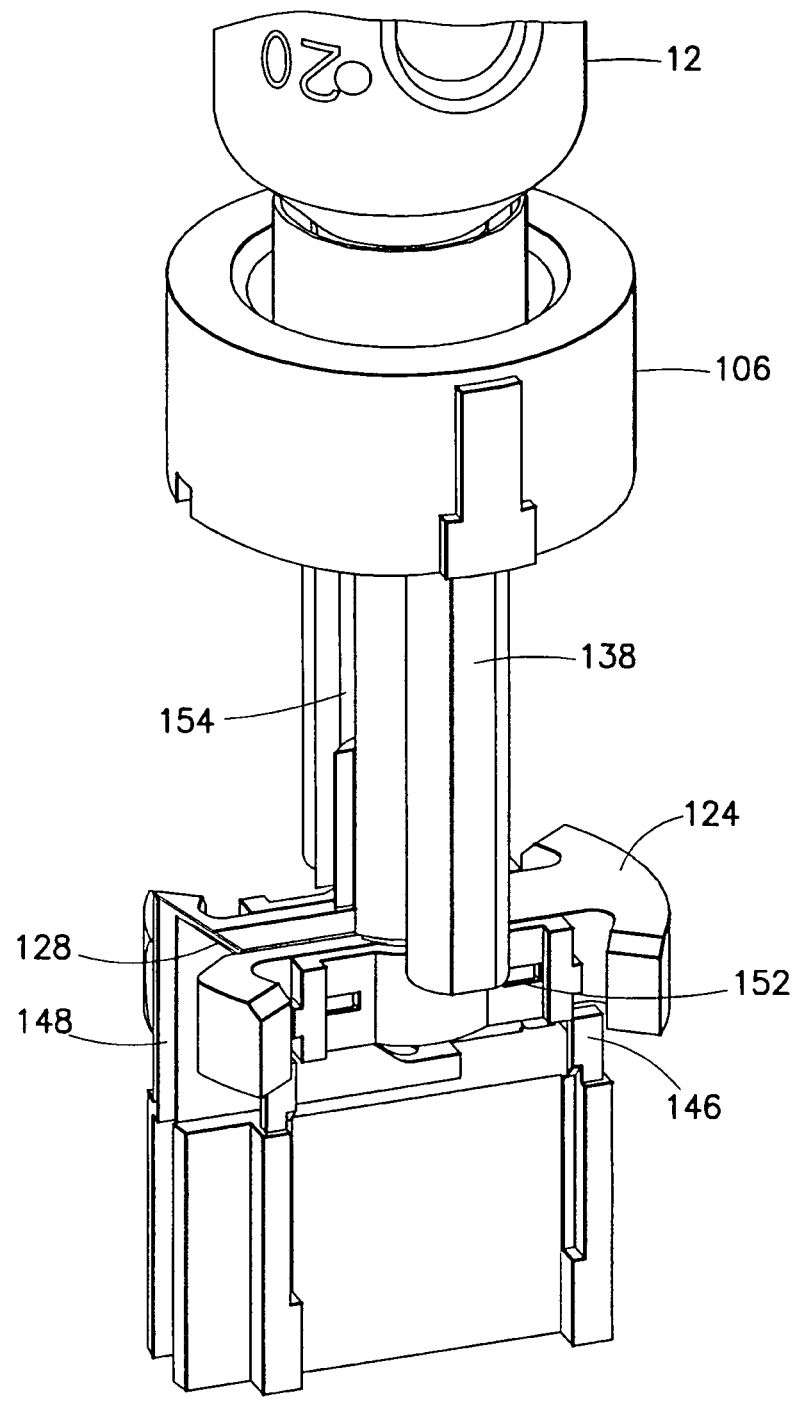
Figure 10D:
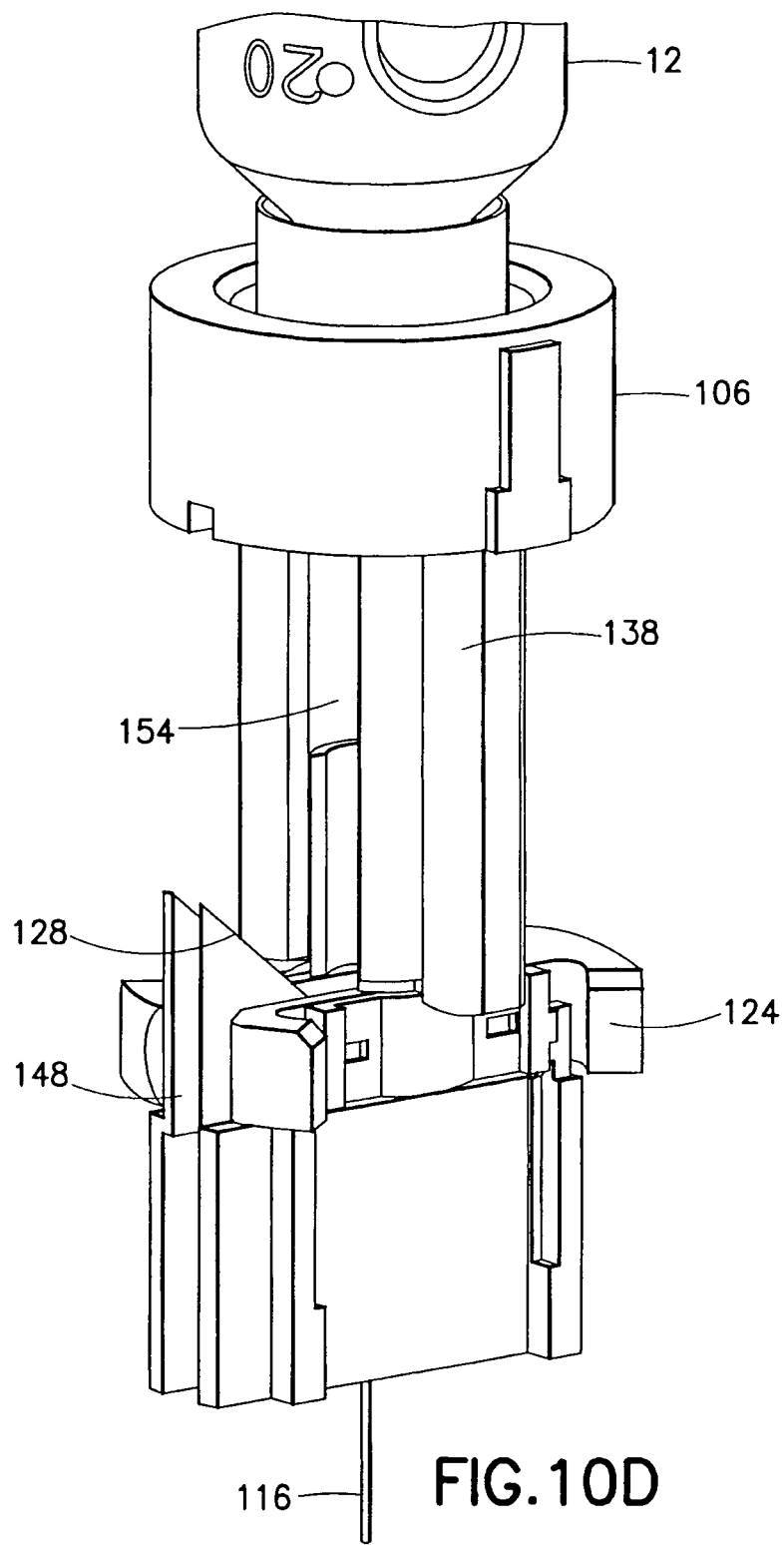

FIGS. 10A-10D are enlarged perspective views of an exemplary ramp and ramp engagement of the ramp-type needle changing assembly of FIG. 3, illustrating stages of use according to an exemplary embodiment of the present invention. FIG. 10A illustrates an exemplary ramp 128 and ramp posts 144 and 146 which release the passive snaps between the needle tray 124 and the vertical opening passageway 138. FIG. 10B shows the exemplary ramp 128 and ramp posts 144 and 146 as first engaging the needle and needle hub 112 within the needle tray 124. A slot 148 is provided in the ramp to permit alignment and ease of travel of the needle and needle hub 112 along the inclined surface of the ramp 128. FIG. 10C shows the engagement of the ramp 128 and ramp posts 144 and 146 releasing the passive snaps 152 once the needle and needle hub 112 have reached the axial position. That is, once the shuttle 122 reaches the bottom of the ramp 142, posts 144 and 146 of the ramp release the passive snaps 152 between the needle tray 124 and the vertical opening passageway 138, allowing the shuttle 122, needle and needle hub 112, and needle tray 124 to be pulled upward and driving the needle through the septum as shown in FIG. 10D.

In the above described or other exemplary embodiments of the present invention, a manual lock can be provided, thereby allowing the user to manually lock the device to allow for safe disposal thereof. Preferably, such lock becomes functional only after the last pen needle has been used. Further, in yet other exemplary embodiments of the present invention, an emergency feature can be provided such that one or more used pen needles can remain accessible for reuse, such that the user has access to at least one pen needle in case of an emergency. In another exemplary embodiment of the present invention, only the last pen needle is always accessible, thereby providing an available pen needle in case of emergency. The other used pen needles can be locked and no longer accessible.

Still further, the rotatable sleeve, retraction feature, or other elements can be provided with a ratchet or other mechanism to prevent reverse rotation or movement, or to prevent rotation or movement beyond a specific point, such as occurring when all the needles have been used.

In the exemplary embodiments of the present invention, the attachable needle storage devices 100 and 200 can be constructed of one or more of a polycarbonate, polyethylene, polypropylene or acrylonitrile butadiene styrene material, but the invention is not limited thereto. The leaf spring can be constructed of any suitable metal or plastic material, such as stainless steel. Further, one or more of the main body 102 and sleeve 104 and/or caps thereof can be color-coded to simplify identification of the new pen needles stored therein.

Currently there are no fully automatic needle changing devices known to be on the market. There are examples of devices that aid with individual steps of the needle changing process, including needle storage, attachment, removal, and disposal; however, none of these devices integrate the needle changing processes into one device. Accordingly, the exemplary embodiments of the present invention, described above, can provide a system and method for storing the enclosed needles around the circumference of the pen, such that it is possible for users to avoid carrying bulky injection "kits". With an integrated device, all needles can be stored with the pen. In addition, the device can store new needles in a sterile manner, utilizing sterility barriers over both sides of the needles, which allows storage of used needles alongside the new ones. Therefore, the device can also be used as a used sharps container.

Cumbersome and potentially dangerous needle attachment is made easier for the user, and the device interfaces are more user friendly than those associated with the typical pen needle hub. Through the provision of such a system and method, the user interfaces with a dial, advancing new needles with a twist, and piercing the septum with a pull upwards. Currently, the user must remove the top of the needle container, twist the needle onto the pen, remove the needle container, and then finally remove a needle cap. While there are some needle storage devices that aid in placing the needle hub on the pen, the user still must remove needle hub packaging, including the inner needle sheath, to place a needle hub onto a typical insulin pen. With the exemplary embodiments of the present invention, the typical four meticulous steps associated with installing small sharp needle hubs can be reduced to two intuitive steps with ergonomic user interfaces.

Needle removal and disposal can also be simplified with the exemplary embodiments of the present invention. There are many devices that aid in removing needles from pens after use, including needle clipping devices and sharps containers that pull the needle from the pen body; however, these devices are more cumbersome when compared to the exemplary embodiments of the present invention. The exemplary embodiments of the present invention can include an automated removal step. By including a needle shield, the device would be able to remove the needle from the septum after delivery and place it in used needle storage without any user input.

Pen needles can be manufactured in existing processes and subsequently, assembled into the device of the exemplary embodiments of the present invention, thereby simplifying the manufacturing process. The overall size of the exemplary embodiments of the present invention can be minimized by allowing used pen needles to be stored in substantially the same spaces previously used to store the unused needles.

Further, the exemplary embodiments of the present invention can be constructed having a size, shape and contour to increase the comfort of the user during transportation, such as in a user's pocket.

The foregoing embodiments and advantages are merely exemplary and are not to be construed as limiting the scope of the present invention. Various modifications, alternatives and variations will be apparent to those of ordinary skill in the art, and are intended to fall within the scope of the invention as defined in the appended claims and their equivalents.

What is claimed is:

1. An attachable needle storage device, comprising:
   a main body, configured to releasably couple with an injection device;
   a rotatable sleeve, configured to releasably store a plurality of needles and position a needle at a radial position within said main body when rotated and displace said needle at said radial position from said rotatable sleeve toward an axial position when rotated further;
   a detent to releasably secure said main body and said rotatable sleeve at a proximal position; and
   a main body spring configured to urge said main body and said rotatable sleeve in a distal direction when releasably secured by said detent,
   wherein said main body is configured to move said needle further from said radial position to said axial position when said main body and said rotatable sleeve are moved in a linear proximal direction.

2. The attachable needle storage device of claim 1, wherein said main body and said rotatable sleeve are configured to move said needle in a proximal direction when said main body and said rotatable sleeve are moved in said linear proximal direction.

3. The attachable needle storage device of claim 1, further comprising:
   a rotatable disc configured to releasably secure said plurality of needles and transport a needle of said plurality to said radial position; and
   a shuttle for receiving a needle from said rotatable disc and transport said needle to said axial position.

4. The attachable needle storage device of claim 3, further comprising a sleeve spring to deflect said needle from said rotatable disc onto said shuttle when said rotatable sleeve is turned.

5. The attachable needle storage device of claim 3, further comprising a ramp to deflect said shuttle from said radial position to said axial position when said main body and said rotatable sleeve are moved in said linear proximal direction.

6. The attachable needle storage device of claim 5, further comprising:
   a securing feature for preventing said shuttle from linear movement until positioned in said axial position;
   wherein said ramp is configured to release said securing feature when said shuttle is positioned in said axial position.

7. The attachable needle storage device of claim 1, wherein said needle is configured to engage a septum at a proximal end and expose a patient contact portion at a distal end when said main body and said rotatable sleeve are moved in said linear proximal direction.

8. The attachable needle storage device of claim 1, further comprising:
   a shield configured to release said detent, wherein said main body spring is configured to move said main body and said rotatable sleeve from said proximal direction to said distal direction;

a shuttle spring configured to urge said shuttle in a radial direction when released, wherein said shuttle is configured to return said needle to said radial position upon said release.

9. The attachable needle storage device of claim 1, wherein said main body and said rotatable sleeve are configured to attach to a distal end of a pen device.

10. An attachable needle storage device, comprising:
a rotatable disc configured to releasably secure a plurality of needles and transport a needle of said plurality to a radial position within said device when rotated, and displace said needle at said radial position from said rotatable disc toward an axial position when rotated further;
a shuttle for receiving a needle from said rotatable disc and transporting said needle to said axial position within said device; and
a ramp to deflect said shuttle from said radial position to said axial position when said device is moved in a linear proximal direction;
wherein said needle is configured to engage a septum at a proximal end and expose a patient contact portion at a distal end when said device is moved in said linear proximal direction.

11. The attachable needle storage device of claim 10, further comprising:
a detent to releasably secure said device at said linear proximal position; and
a shield configured to release said detent to move said needle from said proximal direction to said distal direction, and wherein said shuttle is configured to return said needle to said radial position upon said release.

12. The attachable needle storage device of claim 10, wherein said main body and said rotatable sleeve are configured to attach to a distal end of a pen device.

13. A method for changing a pen needle using a needle storage device, comprising:
attaching the needle storage device to a distal end of a pen device;
rotating a sleeve of said needle storage device to move a new needle from a radial position on a disc when rotated, and toward an axial position and onto a shuttle within said needle storage device when rotated further;
pulling said needle storage device in a proximal direction to move said needle horizontally further toward said axial position of a pen body; and
continue pulling said needle storage device in said proximal direction to move said needle rearward to engage a septum of said pen body and expose a distal end of said needle.

14. The method of claim 13, further comprising:
engaging a needle shield with said needle storage device to release a used needle, wherein said release moves said used needle in a distal direction as urged by a main body spring, and moves said used needle to a radial position on said disc as urged by a shuttle spring.

15. An attachable needle storage device configured to releasably couple with an injection device, comprising:
a rotatable body, configured to releasably store a plurality of needles and position a needle at a radial position within said body when rotated and displace said needle at said radial position from said rotatable body toward an axial position when rotated further;
a detent to releasably secure said rotatable body at a proximal position; and
a main body spring configured to urge said rotatable body in a distal direction when releasably secured by said detent,
wherein said rotatable body is configured to move said needle further from said radial position to said axial position when said rotatable body is moved in a linear proximal direction.

16. The attachable needle storage device of claim 15, wherein said rotatable body is configured to move said needle in a proximal direction when said rotatable body is moved in said linear proximal direction.

17. The attachable needle storage device of claim 15, wherein said needle is configured to engage a septum at a proximal end and expose a patient contact portion at a distal end when said rotatable body is moved in said linear proximal direction.

18. The attachable needle storage device of claim 15, wherein said rotatable body is configured to attach to a distal end of a pen device.

* * * * *